(12) United States Patent
Kremmidiotis et al.

(10) Patent No.: US 7,667,028 B2
(45) Date of Patent: Feb. 23, 2010

(54) COMPOSITIONS AND METHODS FOR ANGIOGENESIS-RELATED MOLECULES AND TREATMENTS

(75) Inventors: Gabriel Kremmidiotis, Flagstaff Hill (AU); Tina Christine Lavranos, Colonel Light Gardens (AU); Annabell Frances Leske, Allenby Gardens (AU)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 11/659,756

(22) PCT Filed: Aug. 9, 2005

(86) PCT No.: PCT/AU2005/001188

§ 371 (c)(1),
(2), (4) Date: Oct. 23, 2007

(87) PCT Pub. No.: WO2006/015426

PCT Pub. Date: Feb. 16, 2006

(65) Prior Publication Data

US 2008/0119430 A1    May 22, 2008

(30) Foreign Application Priority Data

May 10, 2004   (AU) ............... 2005902344
Aug. 9, 2004   (AU) ............... 2004904441

(51) Int. Cl.
*C07H 21/02*    (2006.01)
*C07H 21/04*    (2006.01)
(52) U.S. Cl. .................... 536/24.5; 536/23.1; 536/24.3; 536/24.33
(58) Field of Classification Search ............... 536/23.1, 536/24.3, 24.33, 24.5
See application file for complete search history.

(56) References Cited

U.S. PATENT DOCUMENTS 6,943,241 B2 * 9/2005 Isogai et al. ............... 536/23.1

FOREIGN PATENT DOCUMENTS

WO    WO 03/027285 A    4/2003

OTHER PUBLICATIONS

BionomicBIO2004 presentation, presented Jun. 9, 2004.*
Katoh et al. (International Journal of Molecular Medicine, 2004 vol. 14:333-338).*
Weimann et al. *Towards a catalog of human genes and proteins: sequencing and analysis of 500 novel complete protein coding human cDNAs. Genome Research*, vol. 11, (2001), pp. 422-435.
Written Opinion of the International Searching Authority corresponding to the PCT application No. PCT/AU05/01188 dated Oct. 10, 2005.
International Preliminary Report on Patentability corresponding to the PCT application No. PCT/AU05/01188 dated Feb. 13, 2007.
International Search Report corresponding to the PCT application No. PCT/AU05/01188 dated Oct. 10, 2005.
Altschul et al. *Gapped BLAST and PSI-BLAST: a new generation of protein database search programs. Nucleic Acids Research*, vol. 25, No. 17, (1997), pp. 3389-3402.

(Continued)

*Primary Examiner*—JD Schultz
*Assistant Examiner*—Terra Cotta Gibbs
(74) *Attorney, Agent, or Firm*—Jenkins, Wilson, Taylor & Hunt, P.A.

(57) ABSTRACT

Short interfering RNA (siRNA) molecules which modulate the expression of an angiogenesis-related gene by RNA interference are described. Short hairpin RNA (shRNA) molecules comprising said siRNA molecules are also described. These molecules can target all, or specific, isoforms of the gene. The use of these molecules and of isoforms of the gene for the treatment and diagnosis of angiogenesis-related disorders is also described.

6 Claims, 17 Drawing Sheets

OTHER PUBLICATIONS

Augustin, Hellmut G. *Antiangiogenic tumour therapy: will it work?* TiPS, vol. 19, (1998), pp. 216-222.

Barrett et al. *The structure of the GTPase-activating domain from p50rhoGAP.* Nature, vol. 385, (1997), pp. 458-461.

Bayless et al. *The Cdc-42 and Rac1 GTPases are required for capillary lumen formation in three-dimensional extracellular matrices.* Journal of Cell Science, vol. 115, (2002), pp. 1123-1136.

Breaker et al. *A DNA enzyme with Mg2+-dependent RNA phosphoesterase activity.* Chemistry and Biology, vol. 2, (1995), pp. 655-660.

Chrzanowska-Wodnicka et al. *Rho-stimulated contractility drives the formation of stress fibers and focal adhesions.* The Journal of Cell Biology, vol. 133, No. 6, (1996), pp. 1403-1415.

Cole et al. *Human monoclonal antibodies.* Molecular and Cellular Biochemistry, vol. 62, (1984), pp. 109-120.

Cote et al. *Generation of human monoclonal antibodies reactive with cellular antigens.* Proceedings of the National Academy of Sciences of USA, vol. 80, (1983), pp. 2026-2030.

Etienne-Manneville et al. *Rho GRPases in cell biology.* Nature, vol. 420, (2002), pp. 629-635.

Gamble et al. *Regulation of in vitro capillary tube formation by anti-integrin antibodies.* The Journal of Cell Biology, vol. 121, No. 4, (1993), pp. 931-943.

Gamble et al. *B1 integrin activation inhibits in vitro tube formation: effects on cell migration, vacuole coalescence and lumen formation.* Endothelium, vol. 7, No. 1, (1999), pp. 23-34.

Goldman et al. *In vitro and in vivo gene delivery mediated by a synthetic polycationic amino polymer.* Nature Biotechnology, vol. 15, (1997), pp. 462-466.

Green et al. *Antigen-specific human monoclonal antibodies from mice engineered with human Ig heavy and light chain YACs.* Nature Genetics, vol. 7, (1994), pp. 13-21.

Hanahan, Douglas. *Signaling vascular morphogenesis and maintenance.* Science, vol. 277, No. 5322, (1997), pp. 48-50.

Maisonpierre et al. *Angiopoietin-2, a natural antagonist for Tie2 that disrupts in vivo angiogenesis.* Science, vol. 277, (1997), pp. 55-60.

Haseloff et al. *Simple RNA enzymes with new and highly specific endoribonuclease activities.* Nature, vol. 334, (1988), pp. 585-591.

Heller at al. *Discovery and analysis of inflammatory disease-related genes using cDNA microarrays.* Proceedings of the National Academy of Sciences of USA, vol. 94, (1997), pp. 2150-2155.

Hippenstiel et al. *Rho protein inactivation induced apoptosis of cultured human endothelial cells.* American Journal of Physiology—Lung Cellular and Molecular Physiology, vol. 283, (2002), pp. L830-L838.

Huse et al. *Generation of a large combinatorial library of the immunoglobulin repertoire in phage lambda.* Science, vol. 246, (1989), pp. 1275-1281.

Kohler et al. *Continuous cultures of fused cells secreting antibody of predefined specificity.* Nature, vol. 256, (1975), pp. 495-497.

Kozbor et al. *Specific immunoglobulin production and enhanced tumorigenicity following ascites growth of human hybridomas.* Journal of Immunological Methods, vol. 81, (1985), pp. 31-42.

Lonberg et al. *Antigen-specific human antibodies from mice comprising four distinct genetic modifications.* Nature, vol. 368, (1994), pp. 856-859.

Mackay et al. *Rho GRPases.* The Journal of Biological Chemistry, vol. 273, No. 33, (1998), pp. 20685-20688.

Meyer et al. *Lumen formation during angiogenesis in vitro involves phagocytic activity, formation and secretion of vacuoles, cell death, and capillary tube remodeling by different populations of endothelial cells.* The Anatomical Record, vol. 249, (1997), pp. 327-340.

Musacchio et al. *Crystal structure of the breakpoint cluster region-homology domain from phosphoinositide 3-kinase p85 α subunit.* Proceedings of the National Academy of Sciences of USA, vol. 93, (1996), pp. 14373-14378.

Nobes et al. *Rho GRPases control polarity, protrusion, and adhesion during cell movement.* The Journal of Cell Biology, vol. 144, No. 6, (1999), pp. 1235-1244.

Orlandi et al. *Cloning immunoglobulin variable domains for expression by the polymerase chain reaction.* Proceedings of the National Academy of Sciences of USA, vol. 86, (1989), pp. 3833-3837.

Rickert et al. *B lymphocyte-specific, cre-mediated mutagenesis in mice.* Nucleic Acids Research, vol. 25, No. 6, (1997), pp. 1317-1318.

Rittinger et al. *Structure at 1.65 A of RhoA and its GRPase-activating protein in complex with a transition-state analogue.* Nature, vol. 389, (1997), pp. 758-762.

Scharf et al. *6 heat stress promoters and transcription factors.* Results and Problems in Cell Differentiation, vol. 20, (1994), pp. 125-162.

Schena et al. *Parallel human genome analysis: Microarray-based expression monitoring of 1000 genes.* Proceedings of the National Academy of Sciences of USA, vol. 93, (1996), pp. 10614-10619.

Schwenk et al. *A cre-transgenic mouse strain for the ubiquitous deletion of loxP-flanked gene segments including deletion in germ cells.* Nucleic Acids Research, vol. 23, No. 24, (1995), pp. 5080-5081.

Van Aelst et al. *Rho GRPases and signaling networks.* Genes and Development, vol. 11, (1997), pp. 2295-2322.

Winter et al. *Man-made antibodies.* Nature, vol. 349, (1991), pp. 293-299.

Wojciak-Stothard et al. *Rho and Rac but not Cdc42 regulate endothelial cell permeability.* Journal of Cell Science, vol. 114, (2001), pp. 1343-1355.

* cited by examiner

Figure 3
Active Rho 
Total Lysate 
Active Cdc42 
Total Lysate 
Active Rac 
Total Lysate 
Active Rho 
Total Lysate 

Figure 5
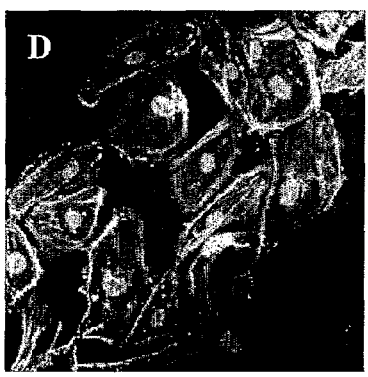
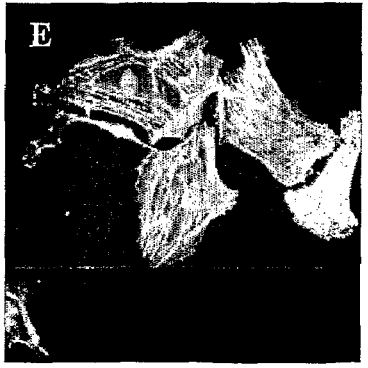

Figure 10
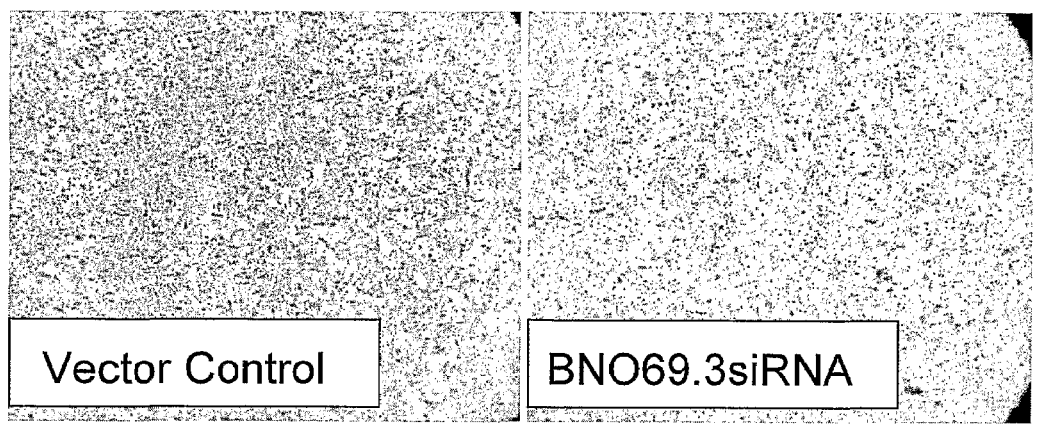
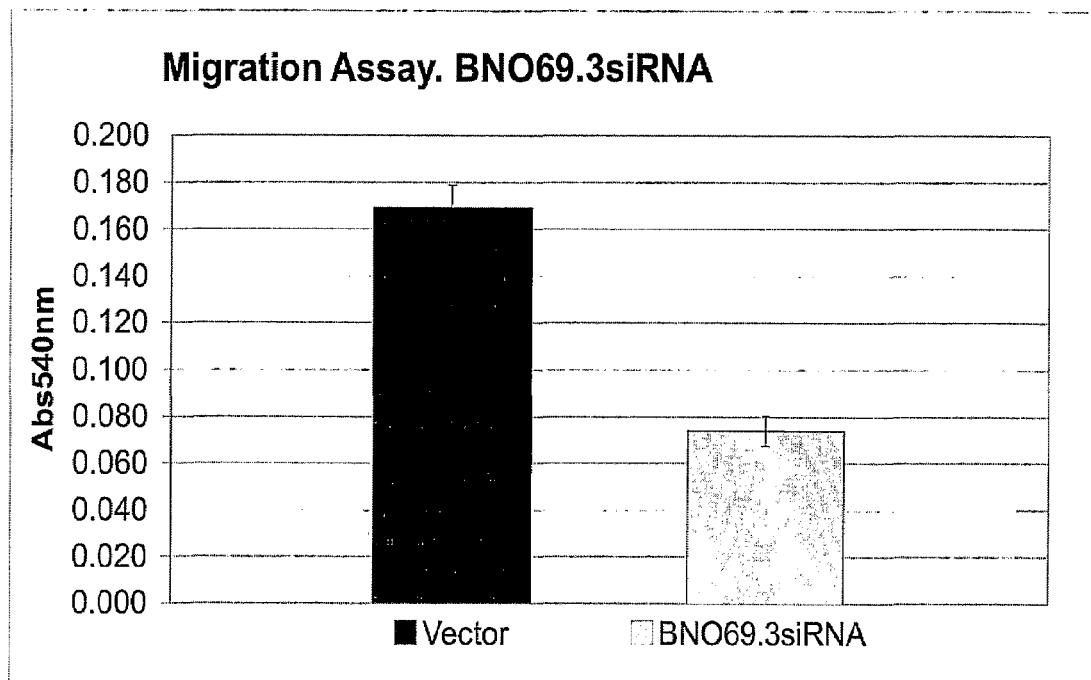

Figure 12

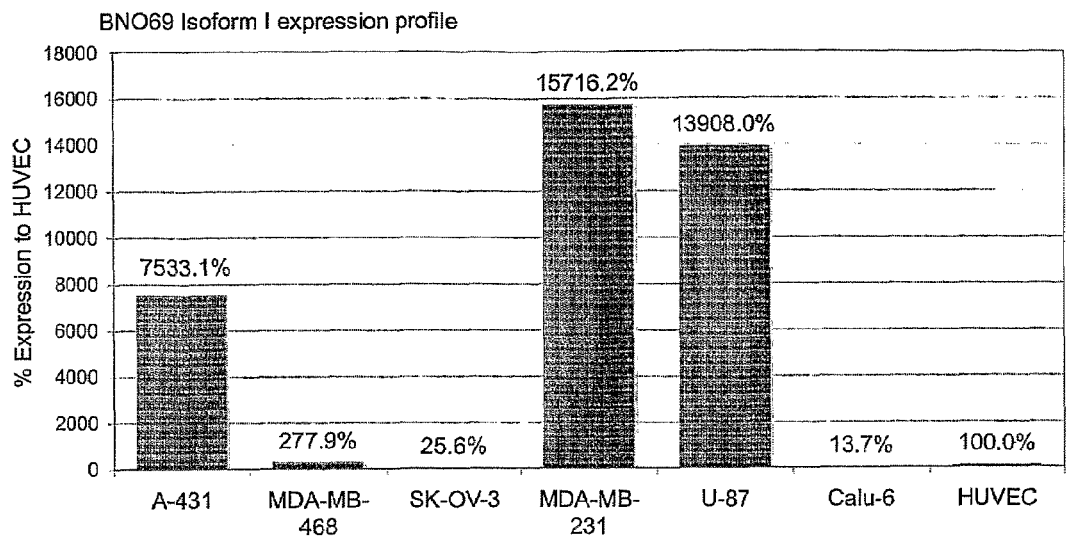

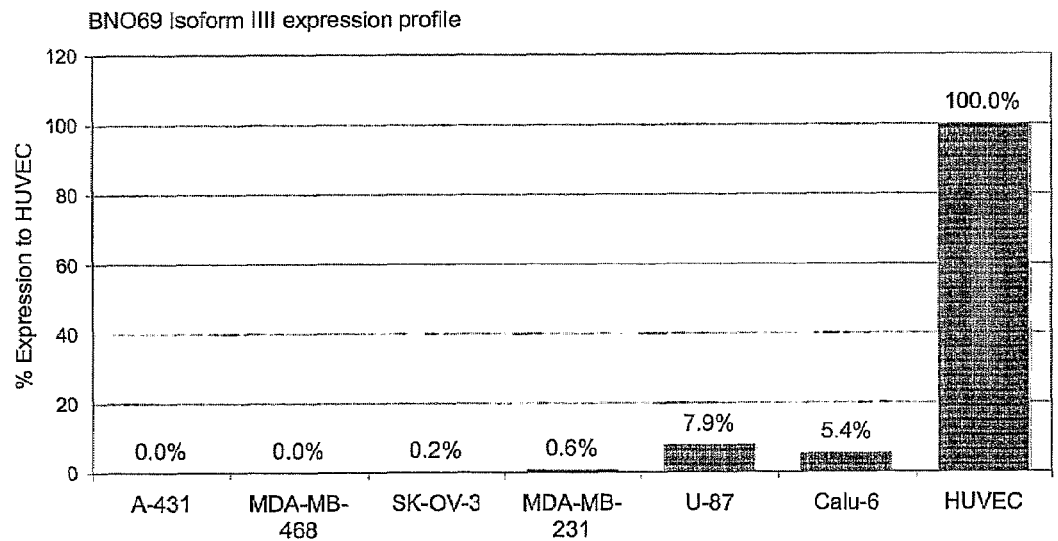

| Cell type | ATCC Number | Description | Media | Supplements |
|---|---|---|---|---|
| MDA-MB-231 | HTB-26 | Breast mammary gland; adenocarcenoma. Obtained from metastatic site; pleural effusion | RPMI-1640 | 10% fetal calf serum PSG |
| A-431 | CRL-1555 | Skin; epidermoid carcinoma Solid tumor isolate | DMEM-F12 | 10% fetal calf serum PSG |
| Calu-6 | HTB-56 | Undefined tissue type propably lung; Anaplastic carcinmona | EMEM | 10% fetal calf serum PSG NEAA |
| SK-OV-3 | HTB-77 | Ovarian; acites adenocarcenoma Obtained from metastatic site | DMEM-F12 | 10% fetal calf serum PSG |
| U-87 MG | HTB-14 | Brain astrocytoma; Glioblastoma Solid tumor isolate | EMEM | 10% fetal calf serum PSG, NEAA, Sodium Pyruvate |
| MDA-MB-468 | HTB-132 | Breast mammary gland; adenocarcenoma Obtained from metastatic site; pleural effusion | RPMI-1640 | 10% fetal calf serum PSG |

Figure 14
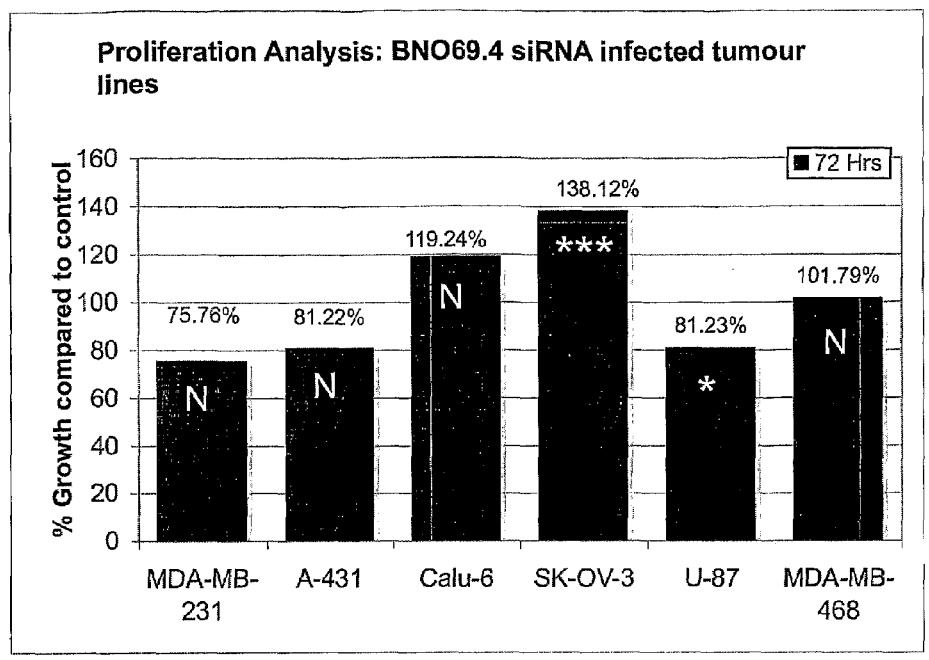
***P < 0.001
**P < 0.01
*P < 0.05
NP > 0.05
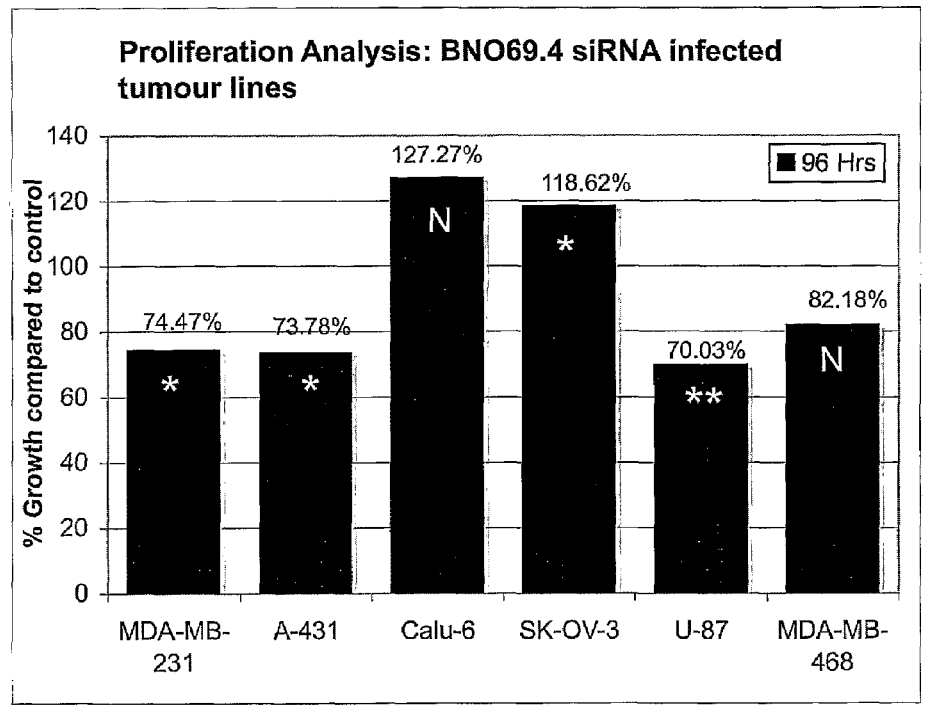

Figure 15
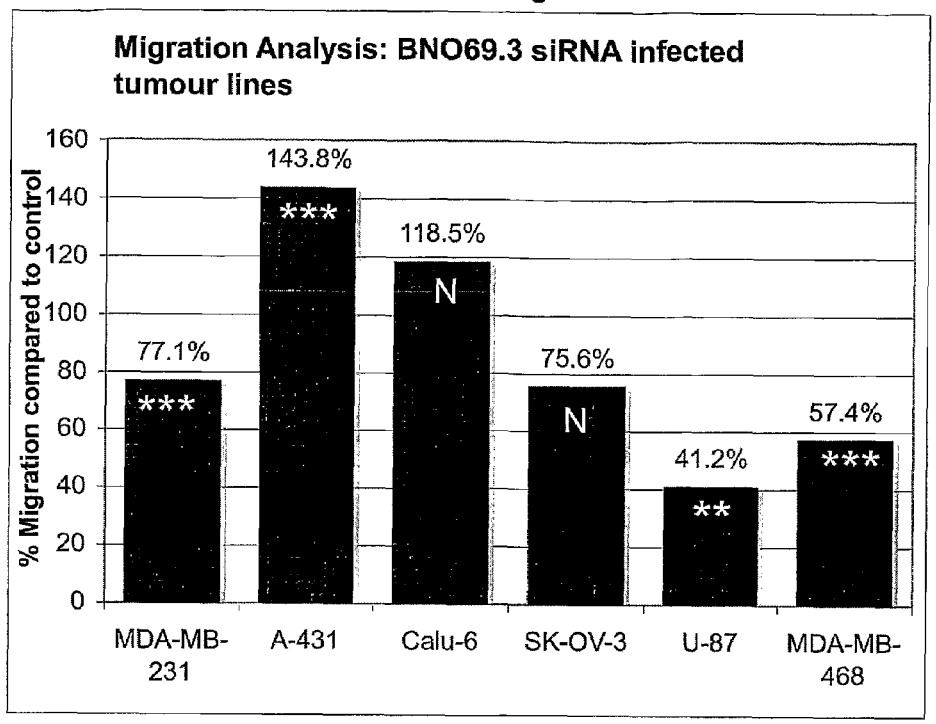
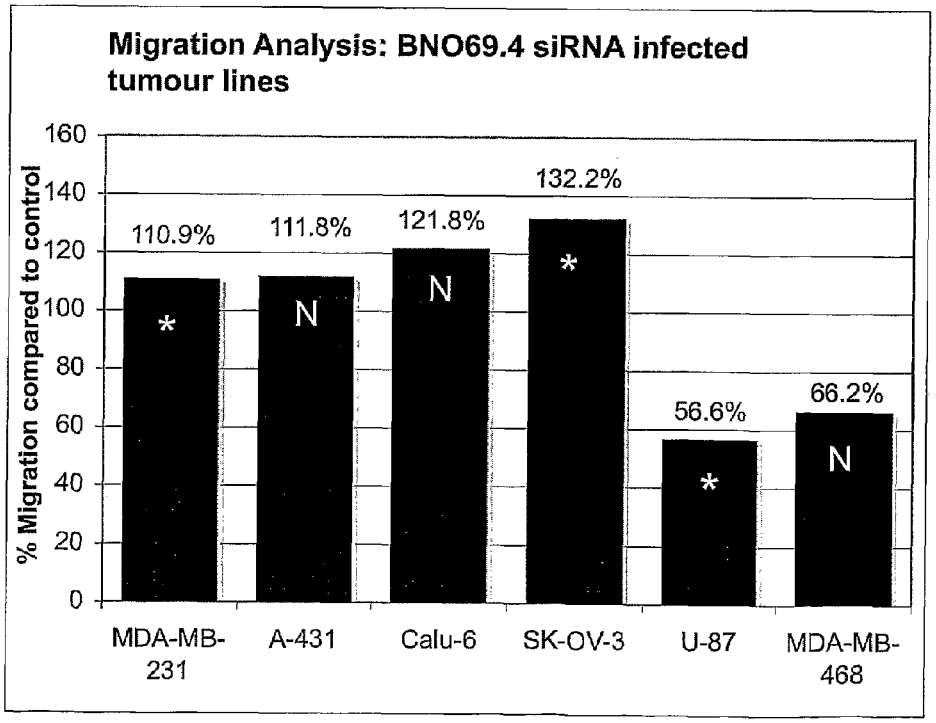
\*\*\* P < 0.001
\*\* P < 0.01
\* P < 0.05
N P > 0.05

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Artificially synthesized BNO69 Isoform I nt
      c1859 - c1877

<400> SEQUENCE: 1
gtagtcgtgc caccagtag                                               19

<210> SEQ ID NO 2
<211> LENGTH: 19
<212> TYPE: DNA
<213> ORGANISM: Artificial Sequence
<220> FEATURE:
<223> OTHER INFORMATION: Artificially synthesized BNO69 Isoform I nt
      c101 - c119

<400> SEQUENCE: 2
agacttggca tactcgctg                                               19

<210> SEQ ID NO 3
<211> LENGTH: 19
<212> TYPE: RNA
<213> ORGANISM: Artificial Sequence
<220> FEATURE:
<223> OTHER INFORMATION: Artificially synthesized siRNA molecule

<400> SEQUENCE: 3
guagucgugc caccaguag                                               19

<210> SEQ ID NO 4
<211> LENGTH: 19
<212> TYPE: RNA
<213> ORGANISM: Artificial Sequence
<220> FEATURE:
<223> OTHER INFORMATION: Artificially synthesized siRNA molecule

<400> SEQUENCE: 4
agacuuggca uacucgcug                                               19

<210> SEQ ID NO 5
<211> LENGTH: 9
<212> TYPE: DNA
<213> ORGANISM: Artificial Sequence
<220> FEATURE:
<223> OTHER INFORMATION: Artificially synthesized linker sequence

<400> SEQUENCE: 5 ttcaagaga                                                           9
```

<210> SEQ ID NO 6
<211> LENGTH: 64
<212> TYPE: DNA
<213> ORGANISM: Artificial Sequence
<220> FEATURE:
<223> OTHER INFORMATION: Artificially synthesized shRNA molecule

<400> SEQUENCE: 6
gatccccgta gtcgtgccac cagtagttca agagactact ggtggcacga ctacttttg      60 gaaa                                                                  64

<210> SEQ ID NO 7
<211> LENGTH: 63
<212> TYPE: DNA
<213> ORGANISM: Artificial Sequence
<220> FEATURE:
<223> OTHER INFORMATION: Artificially synthesized shRNA molecule

<400> SEQUENCE: 7 gatcccaga cttggcatac tcgctgttca agagcagcga gtatgccaag tcttttttgg      60
aaa                                                                   63

<210> SEQ ID NO 8
<211> LENGTH: 2936
<212> TYPE: DNA
<213> ORGANISM: Homo sapiens

<400> SEQUENCE: 8
ttttctaact tctgggactc tttgcgcaac tgctaggatt tctcaagtgc atgtggcaac      60
acagcccagc tccgggtgga aaccagcagg gctctggagg ggctcggaga ccaggggagc    120
tgtcaaggct gcggcgggga ccagagagga gcctggcggg ggtggctggg tggctggggg    180 aatccccca acttcccatc gcaggcgcag ctctctcggc cgcctatttc ctccgaaacc     240
cgcgctgcgg agcagcccag tgcatagagt tcaacacttc cccttgttgt ggaaagtaaa    300
ggagcctcac taccaccttt ttttctttgc gttttcttac tgctggtcct gggagccttt    360
tccttcggag cagcagccct gtccggcatc tgtcttgagc tgccagcaag gaaagtccat    420
cagcttgata atggaggaga caatgactc cacggagaac ccccaacaag gccaagggcg     480
gcagaatgcc atcaagtgtg ggtggctgag gaagcaagga ggctttgtca agacttggca    540
tactcgctgg tttgtgctca aggggatca gctctattat ttcaaagatg aagatgaaac    600
caagcccttg ggtactattt ttctgcctgg aaataaagtt tctgagcatc cctgcaatga    660
agagaaccca gggaagttcc ttttgaagt agttccagga ggcgatcgag atcggatgac    720
agcaaatcat gagagctacc tcctcatggc aagcacccag aatgatatgg aagactgggt    780
gaagtcaatc cgccgagtca tatggggacc tttcggagga ggcatttttg gacagaaact    840
ggaggatgct gttcgttatg agaagagata tgggaaccgt ctggctccga tgttggtgga    900
gcagtgcgtg gactttatcc gacaaggggg gctgaaagaa gagggtctct ttcgactgcc    960
aggccaggct aatcttgtta aggagctcca agatgccttt gactgtgggg agaagccatc   1020
atttgacagc aacacagatg tacacacggt ggcatcactt cttaagctgt acctccgaga   1080
acttccagaa ccagttattc cttatgcgaa gtatgaagat ttttttgtcat gtgccaaact   1140 gctcagcaag gaagaggaag caggtgttaa ggaattagca aagcaggtga agagtttgcc   1200
agtggtaaat tacaacctcc tcaagtatat ttgcagattc ttggatgaag tacagtccta   1260
ctcgggagtt aacaaaatga gtgtgcagaa cttggcaacg gtctttggtc ctaatatcct   1320

```
gcgccccaaa gtggaagatc ctttgactat catggagggc actgtggtgg tccagcagtt   1380
gatgtcagtg atgattagca acatgattg cctctttccc aaagatgcag aactacaaag    1440
caagccccaa gatggagtga gcaacaacaa cgaaattcag aagaaagcca ccatggggca   1500
gttacagaac aaggagaaca ataacaccaa ggacagccct agtagacagt gctcctggga   1560
caagtctgag tcaccccaga gaagcagcat gaacaatgga tcccccacag ctctatcagg   1620
cagcaaaacc aacagcccaa agaacagtgt tcacaagcta gatgtgtcta gaagccccc    1680 tctcatggtc aaaagaacc cagcctttaa taagggtagt gggatagtta ccaatgggtc    1740
cttcagcagc agtaatgcag aaggtcttga aaaacccaa accaccccca atgggagcct    1800
acaggccaga aggagctctt cactgaaggt atctggtacc aaaatgggca cgcacagtgt    1860
acagaatgga acggtgcgca tgggcatttt gaacagcgac acactcggga accccacaaa    1920
tgttcgaaac atgagctggc tgccaaatgg ctatgtgacc ctgagggata caagcagaa     1980 agaacaagct ggagagttag ccagcacaca cagactgtcc acctatgata atgtccatca     2040
acagttctcc atgatgaacc ttgatgacaa gcagagcatt gacagtgcta cctggtccac     2100
ttcctcctgt gaaatctccc tccctgagaa ctccaactcc tgtcgctctt ctaccaccac     2160
ctgcccagag caagactttt ttgggggaa ctttgaggac cctgttttgg atgggccccc      2220
gcaggacgac ctttcccacc ccagggacta tgaaagcaaa agtgaccaca ggagtgtggg     2280
aggtcgaagt agtcgtgcca ccagtagcag tgacaacagt gagacatttg tgggcaacag     2340
cagcagcaac cacagtgcac tgcacagttt agtttccagc ctgaaacagg aaatgaccaa     2400
acagaagata gagtatgagt ccaggataaa gagcttagaa cagcgaaact tgactttgga     2460
aacagaaatg atgagcctcc atgatgaact ggatcaggag aggaaaaagt tcacaatgat     2520
agaaataaaa atgcgaaatg ccgagcgagc aaaagaagat gccgagaaaa gaaatgacat     2580
gctacagaaa gaagtggagc agtttttttc cacgtttgga gaactgacag tggaacccag     2640
gagaaccgag agaggaaaca caatatggat tcagtgagcc tgctttcgcc tgctgtctct     2700
gatggctctg gcaaggactc cagggattct ggtgggatat gacttagaac caggtggctg     2760
gtcacctgga tgtacagaag tctaactggt gaaggaatat catttacaga cattaaacat     2820
ccatatctgc aatgtgtacc aaagttatat catgccccat aatgctactg tcaagtgtta     2880
caactggata tgtgtatata gagtagtttt tcaaaagtaa actaaaaatg agaagc         2936
```

<210> SEQ ID NO 9
<211> LENGTH: 748
<212> TYPE: PRT
<213> ORGANISM: Homo sapiens

<400> SEQUENCE: 9

```
Met Glu Glu Asn Asn Asp Ser Thr Glu Asn Pro Gln Gln Gly Gln Gly
1               5                   10                  15

Arg Gln Asn Ala Ile Lys Cys Gly Trp Leu Arg Lys Gln Gly Gly Phe
            20                  25                  30

Val Lys Thr Trp His Thr Arg Trp Phe Val Leu Lys Gly Asp Gln Leu
        35                  40                  45

Tyr Tyr Phe Lys Asp Glu Asp Glu Thr Lys Pro Leu Gly Thr Ile Phe
    50                  55                  60

Leu Pro Gly Asn Lys Val Ser Glu His Pro Cys Asn Glu Glu Asn Pro
65                  70                  75                  80

Gly Lys Phe Leu Phe Glu Val Val Pro Gly Gly Asp Arg Asp Arg Met
                85                  90                  95
```

-continued

Thr Ala Asn His Glu Ser Tyr Leu Leu Met Ala Ser Thr Gln Asn Asp
            100                 105                 110

Met Glu Asp Trp Val Lys Ser Ile Arg Arg Val Ile Trp Gly Pro Phe
        115                 120                 125

Gly Gly Gly Ile Phe Gly Gln Lys Leu Glu Asp Ala Val Arg Tyr Glu
    130                 135                 140

Lys Arg Tyr Gly Asn Arg Leu Ala Pro Met Leu Val Glu Gln Cys Val
145                 150                 155                 160

Asp Phe Ile Arg Gln Arg Gly Leu Lys Glu Glu Gly Leu Phe Arg Leu
                165                 170                 175

Pro Gly Gln Ala Asn Leu Val Lys Glu Leu Gln Asp Ala Phe Asp Cys
            180                 185                 190

Gly Glu Lys Pro Ser Phe Asp Ser Asn Thr Asp Val His Thr Val Ala
        195                 200                 205

Ser Leu Leu Lys Leu Tyr Leu Arg Glu Leu Pro Glu Pro Val Ile Pro
    210                 215                 220

Tyr Ala Lys Tyr Glu Asp Phe Leu Ser Cys Ala Lys Leu Leu Ser Lys
225                 230                 235                 240

Glu Glu Glu Ala Gly Val Lys Glu Leu Ala Lys Gln Val Lys Ser Leu
                245                 250                 255

Pro Val Val Asn Tyr Asn Leu Leu Lys Tyr Ile Cys Arg Phe Leu Asp
            260                 265                 270

Glu Val Gln Ser Tyr Ser Gly Val Asn Lys Met Ser Val Gln Asn Leu
        275                 280                 285

Ala Thr Val Phe Gly Pro Asn Ile Leu Arg Pro Lys Val Glu Asp Pro
    290                 295                 300

Leu Thr Ile Met Glu Gly Thr Val Val Val Gln Gln Leu Met Ser Val
305                 310                 315                 320

Met Ile Ser Lys His Asp Cys Leu Phe Pro Lys Asp Ala Glu Leu Gln
                325                 330                 335

Ser Lys Pro Gln Asp Gly Val Ser Asn Asn Asn Glu Ile Gln Lys Lys
            340                 345                 350

Ala Thr Met Gly Gln Leu Gln Asn Lys Glu Asn Asn Thr Lys Asp
        355                 360                 365

Ser Pro Ser Arg Gln Cys Ser Trp Asp Lys Ser Glu Ser Pro Gln Arg
    370                 375                 380

Ser Ser Met Asn Asn Gly Ser Pro Thr Ala Leu Ser Gly Ser Lys Thr
385                 390                 395                 400

Asn Ser Pro Lys Asn Ser Val His Lys Leu Asp Val Ser Arg Ser Pro
                405                 410                 415

Pro Leu Met Val Lys Lys Asn Pro Ala Phe Asn Lys Gly Ser Gly Ile
            420                 425                 430

Val Thr Asn Gly Ser Phe Ser Ser Asn Ala Glu Gly Leu Glu Lys
        435                 440                 445

Thr Gln Thr Thr Pro Asn Gly Ser Leu Gln Ala Arg Arg Ser Ser Ser
    450                 455                 460

Leu Lys Val Ser Gly Thr Lys Met Gly Thr His Ser Val Gln Asn Gly
465                 470                 475                 480

Thr Val Arg Met Gly Ile Leu Asn Ser Asp Thr Leu Gly Asn Pro Thr
                485                 490                 495

Asn Val Arg Asn Met Ser Trp Leu Pro Asn Gly Tyr Val Thr Leu Arg
            500                 505                 510

-continued

```
Asp Asn Lys Gln Lys Glu Gln Ala Gly Glu Leu Gly Gln His Asn Arg
        515                 520                 525

Leu Ser Thr Tyr Asp Asn Val His Gln Gln Phe Ser Met Met Asn Leu
    530                 535                 540

Asp Asp Lys Gln Ser Ile Asp Ser Ala Thr Trp Ser Thr Ser Ser Cys
545                 550                 555                 560

Glu Ile Ser Leu Pro Glu Asn Ser Asn Ser Cys Arg Ser Ser Thr Thr
                565                 570                 575

Thr Cys Pro Glu Gln Asp Phe Phe Gly Gly Asn Phe Glu Asp Pro Val
            580                 585                 590

Leu Asp Gly Pro Pro Gln Asp Leu Ser His Pro Arg Asp Tyr Glu
        595                 600                 605

Ser Lys Ser Asp His Arg Ser Val Gly Gly Arg Ser Ser Arg Ala Thr
    610                 615                 620

Ser Ser Ser Asp Asn Ser Glu Thr Phe Val Gly Asn Ser Ser Ser Asn
625                 630                 635                 640

His Ser Ala Leu His Ser Leu Val Ser Ser Leu Lys Gln Glu Met Thr
                645                 650                 655

Lys Gln Lys Ile Glu Tyr Glu Ser Arg Ile Lys Ser Leu Glu Gln Arg
            660                 665                 670

Asn Leu Thr Leu Glu Thr Glu Met Met Ser Leu His Asp Glu Leu Asp
        675                 680                 685

Gln Glu Arg Lys Lys Phe Thr Met Ile Glu Ile Lys Met Arg Asn Ala
    690                 695                 700

Glu Arg Ala Lys Glu Asp Ala Glu Lys Arg Asn Asp Met Leu Gln Lys
705                 710                 715                 720

Glu Val Glu Gln Phe Phe Ser Thr Phe Gly Glu Leu Thr Val Glu Pro
                725                 730                 735

Arg Arg Thr Glu Arg Gly Asn Thr Ile Trp Ile Gln
            740                 745
```

<210> SEQ ID NO 10
<211> LENGTH: 4593
<212> TYPE: DNA
<213> ORGANISM: Homo sapiens

<400> SEQUENCE: 10

| | | | | |
|---|---|---|---|---|
| gggggagttt | gaagacagaa | aggaaagggg | agaaacctgc | agagagcatc aaaggatggg | 60 |
| gggtgctata | aaagaagcag | gggggtcctt | tgaaagaaat | ctatcatgca ctgaaatgct | 120 |
| ttctggagaa | ggtgccgtta | ttttcctccc | ctcttgctca | gatgaaagga gccagcaagg | 180 |
| acagtcctga | aatattcctc | aggggacttt | ttgtcattgt | tcctctttcc tcttgcacag | 240 |
| agctatttgc | tgacctttcc | agaggaatct | cagtccagct | gagaagacag ttcttaataa | 300 |
| aaacaaaaaa | atgcaaaaac | caattcctgc | tgtttgaatg | ggaatggtag cttgcttgct | 360 |
| gcagttcttt | tcctgtgaca | ttttggaatg | tctgcagaaa | cttaaaaaaa agaaaaaaaa | 420 |
| aaccttaaaa | actccctgga | ttaggcaaga | gaaaggaag | ttttttttg ctaaacagga | 480 |
| gtaaatgaga | ggtggtaact | tatccctaag | ccaggacctg | gatgatcaaa accttcaaat | 540 |
| tctagggatc | agcacttcaa | aaataacaag | taaacaagca | tgaggagtgg ctgttgggtt | 600 |
| tcgctcagag | gcaggtttta | aaggaagcca | aaacggggtt | cagaacttca ggcctgtacg | 660 |
| atgcctgaag | accggaattc | tggggggtgc | ccggctggtg | ccttagcctc aactcctttc | 720 |
| atccctaaaa | ctacatacag | aagaatcaaa | cggtgtttta | gttttcggaa aggcattttt | 780 |

```
ggacagaaac tggaggatac tgttcgttat gagaagagat atgggaaccg tctggctccg     840
atgttggtgg agcagtgcgt ggactttatc cgacaaaggg ggctgaaaga agagggtctc     900
tttcgactgc caggccaggc taatcttgtt aaggagctcc aagatgcctt tgactgtggg     960
gagaagccat catttgacag caacacagat gtacacacgt ggcatcact tcttaagctg    1020 tacctccgag aacttccaga accagttatt ccttatgcga agtatgaaga ttttttgtca    1080
tgtgccaaac tgctcagcaa ggaagaggaa gcaggtgtta aggaattagc aaagcaggtg    1140
aagagtttgc cagtggtaaa ttacaacctc ctcaagtata tttgcagatt cttggatgaa    1200
gtacagtcct actcgggagt taacaaaatg agtgtgcaga acttggcaac ggtctttggt    1260
cctaatatcc tgcgcccaa agtggaagat cctttgacta tcatggaggg cactgtggtg    1320
gtccagcagt tgatgtcagt gatgattagc aaacatgatt gcctctttcc caaagatgca    1380
gaactacaaa gcaagcccca agatggagtg agcaacaaca atgaaattca gaagaaagcc    1440
accatggggc tgttacagaa caaggagaac aataacacca aggacagccc tagtaggcag    1500
tgctcctggg acaagtctga gtcaccccag agaagcagca tgaacaatgg atcccccaca    1560
gctctatcag gcagcaaaac caacagccca aagaacagtg ttcacaagct agatgtgtct    1620
agaagccccc ctctcatggt caaaaagaac ccagccttta taagggtag tgggatagtt    1680 accaatgggt ccttcagcag cagtaatgca gaaggtcttg agaaaaccca aaccaccccc    1740
aatgggagcc tacaggccag aaggagctct tcactgaagg tatctggtac caaaatgggc    1800
acgcacagtg tacagaatgg aacggtgcgc atgggcattt tgaacagcga cacactcggg    1860
aaccccacaa atgttcgaaa catgagctgg ctgccaaatg gctatgtgac cctgagggat    1920
aacaagcaga aagaacaagc tggagagtta ggccagcaca acagactgtc cacctatgat    1980
aatgtccatc aacagttctc catgatgaac cttgatgaca agcagagcat tgacagtgct    2040
acctggtcca cttcctcctg tgaaatctcc ctccctgaga actccaactc ctgtcgctct    2100
tctaccacca cctgcccaga gcaagacttt ttttggggga ctttgagga ccctgttttg    2160 gatgggcccc cgcaggacga ccttttccac cccagggact atgaaagcaa aagtgaccac    2220
aggagtgtgg gaggtcgaag tagtcgtgcc accagtagca gtgacaacag tgagacattt    2280
gtgggcaaca gcagcagcaa ccacagtgca ctgcacagtt tagtttccag cctgaaacag    2340
gaaatgacca acagaagat agagtatgag tccaggataa agagcttaga acagcgaaac    2400
ttgactttgg aaacagaaat gatgagcctc catgatgaac tggatcagga gaggaaaaag    2460
ttcacaatga tagaaataaa aatgcgaaat gccgagcgag caaaagaaga tgccgagaaa    2520
agaaatgaca tgctacagaa agaaatggag cagttttttt ccacgtttgg agaactgaca    2580
gtggaaccca ggagaaccga gagaggaaac acaatatgga ttcagtgagc ctgctttcgc    2640
ctgctgtctc tgatggctct ggcaaggact ccagggattc tggtgggata tgacttagaa    2700
ccaggtggct ggtcacctgg atgtacagaa gtctaactgg tgaaggaata tcatttacag    2760
acattaaaca tccatatctg caatgtgtac caaagttata tcatgcccca taatgctact    2820
gtcaagtgtt acaactggat atgtgtatat agagtagttt ttcaaaagta aactaaaaat    2880
gagaagcata tttcaagaat tattttattg caagtcttgt atttaaatgt taaatcaata    2940
tgttgttgca atttagcttg cttttcaagct tcacccccttg cacttaacat aagctatttt    3000
tggcattgtg ttatcatcgg cttatttttat agatcaatat ttttatttcc cttttttgct    3060
gaggaaatga agataagcaa aaatataaat atatatataa atatatgagt tattaaaacc    3120
agaagaatac tttgtggctg tgctgtttgt gccaatagac tttgtcatga ccaaaaagag    3180
```

-continued

```
aaatgtaaat agtttttataa aatacagtcg aatcaccagg aacctttgag ctgcttttaa    3240
aattcttccc ctggcaccac tcagttttgc ttttgcgagg cgatttgaca taggaacttt    3300
gagactccat gagaaagtcc ctttctgagg cccactgtct accttgccag atcctcagtg    3360
cgtatcgcca atgcaggatg ctccttagaa aagaaaaaat ggtaaaggat ggcatttaac    3420
gattcaggct ttgaattact ctgtccctct ggaccgaatc tctttaactg ctggatagtt    3480
ttagaggaat tctcctgcta cttaggtact gggaaacaat gcttgctaaa ccatgcccac    3540
gtgagcacct gtctcccact caaacctctc ccatctccca caactgcac tttagaatac     3600
cagcagtgaa atggtattac tgtttccctc tgagtgaaac tgctagagta tatgtcacgt    3660
agtgacattt ttttctcact caggctattg ccatctggga ttctctccct actacagctg    3720
gcaaagttgg tttgcagcaa gaagatagtg ggaggggggcc aggctgcagg agaaggagaa    3780
aagtttagaa gaaacaaacc attttgcttc taattttgac agtatcactt tcctgttaaa    3840
acatacaata attttaaaag gtgaatgcct aaagttccaa ttttagcaaa tatgggaacc    3900
tcagcaatgc taattttcta gaaaaaccca gggctctttg gagctagagt tttgggagaa    3960
cagttcttca caataaggca atggttttga gaggccaggc aaataatctt tctcaccgta    4020
gaacaaaaag ttacaaaagg cataatcgga aatagagact acatacttga gtttatgggg    4080
tttgtgttgt ttgaaggttc aatgcttgca tgtgtttatt tattttcaag agggaaagtg    4140
gtctgtactg ctttcatcct tgccactgtc ttgcttttat tttttactct cccactgagc    4200
aagcgtctgt ggtcctatgg tatcaaccag tatctttata gcaataattt ctttaattcc    4260
cttttctctc tctttccaat tatttaacca gttacttcca cctggacata cgataggaaa    4320
ttcaaactca aaatatgaaa attgatctta ataactctcc cttcatatct tttcacctat    4380
ttccagtcct tatcatagtt gataaaaacc tcagactcat ccagaaagct atatgatgca    4440
ctagtaaaaa aacaaagat atttaaactg cttgggttca aatggtatac aatttgccag     4500
ctgttactga accttctatg cataactttt ttttttcctct gtgcaattgg aataataaaa    4560
atactactcc cataaaaaaa aaaaaaaaa aac                                  4593
```

<210> SEQ ID NO 11
<211> LENGTH: 655
<212> TYPE: PRT
<213> ORGANISM: Homo sapiens

<400> SEQUENCE: 11

Met Pro Glu Asp Arg Asn Ser Gly Gly Cys Pro Ala Gly Ala Leu Ala
1               5                   10                  15

Ser Thr Pro Phe Ile Pro Lys Thr Thr Tyr Arg Arg Ile Lys Arg Cys
            20                  25                  30

Phe Ser Phe Arg Lys Gly Ile Phe Gly Gln Lys Leu Glu Asp Thr Val
        35                  40                  45

Arg Tyr Glu Lys Arg Tyr Gly Asn Arg Leu Ala Pro Met Leu Val Glu
    50                  55                  60

Gln Cys Val Asp Phe Ile Arg Gln Arg Gly Leu Lys Glu Glu Gly Leu
65                  70                  75                  80

Phe Arg Leu Pro Gly Gln Ala Asn Leu Val Lys Glu Leu Gln Asp Ala
                85                  90                  95

Phe Asp Cys Gly Glu Lys Pro Ser Phe Asp Ser Asn Thr Asp Val His
            100                 105                 110

Thr Val Ala Ser Leu Leu Lys Leu Tyr Leu Arg Glu Leu Pro Glu Pro

```
                115                 120                 125
Val Ile Pro Tyr Ala Lys Tyr Glu Asp Phe Leu Ser Cys Ala Lys Leu
            130                 135                 140

Leu Ser Lys Glu Glu Glu Ala Gly Val Lys Glu Leu Ala Lys Gln Val
145                 150                 155                 160

Lys Ser Leu Pro Val Val Asn Tyr Asn Leu Leu Lys Tyr Ile Cys Arg
                165                 170                 175

Phe Leu Asp Glu Val Gln Ser Tyr Ser Gly Val Asn Lys Met Ser Val
            180                 185                 190

Gln Asn Leu Ala Thr Val Phe Gly Pro Asn Ile Leu Arg Pro Lys Val
            195                 200                 205

Glu Asp Pro Leu Thr Ile Met Glu Gly Thr Val Val Gln Gln Leu
210                 215                 220

Met Ser Val Met Ile Ser Lys His Asp Cys Leu Phe Pro Lys Asp Ala
225                 230                 235                 240

Glu Leu Gln Ser Lys Pro Gln Asp Gly Val Ser Asn Asn Asn Glu Ile
                245                 250                 255

Gln Lys Lys Ala Thr Met Gly Leu Leu Gln Asn Lys Glu Asn Asn Asn
            260                 265                 270

Thr Lys Asp Ser Pro Ser Arg Gln Cys Ser Trp Asp Lys Ser Glu Ser
            275                 280                 285

Pro Gln Arg Ser Ser Met Asn Asn Gly Ser Pro Thr Ala Leu Ser Gly
            290                 295                 300

Ser Lys Thr Asn Ser Pro Lys Asn Ser Val His Lys Leu Asp Val Ser
305                 310                 315                 320

Arg Ser Pro Pro Leu Met Val Lys Lys Asn Pro Ala Phe Asn Lys Gly
                325                 330                 335

Ser Gly Ile Val Thr Asn Gly Ser Phe Ser Ser Ser Asn Ala Glu Gly
            340                 345                 350

Leu Glu Lys Thr Gln Thr Thr Pro Asn Gly Ser Leu Gln Ala Arg Arg
            355                 360                 365

Ser Ser Ser Leu Lys Val Ser Gly Thr Lys Met Gly Thr His Ser Val
370                 375                 380

Gln Asn Gly Thr Val Arg Met Gly Ile Leu Asn Ser Asp Thr Leu Gly
385                 390                 395                 400

Asn Pro Thr Asn Val Arg Asn Met Ser Trp Leu Pro Asn Gly Tyr Val
                405                 410                 415

Thr Leu Arg Asp Asn Lys Gln Lys Glu Gln Ala Gly Glu Leu Gly Gln
            420                 425                 430

His Asn Arg Leu Ser Thr Tyr Asp Asn Val His Gln Gln Phe Ser Met
            435                 440                 445

Met Asn Leu Asp Asp Lys Gln Ser Ile Asp Ser Ala Thr Trp Ser Thr
450                 455                 460

Ser Ser Cys Glu Ile Ser Leu Pro Glu Asn Ser Asn Ser Cys Arg Ser
465                 470                 475                 480

Ser Thr Thr Thr Cys Pro Glu Gln Asp Phe Phe Gly Gly Asn Phe Glu
                485                 490                 495

Asp Pro Val Leu Asp Gly Pro Pro Gln Asp Asp Leu Ser His Pro Arg
            500                 505                 510

Asp Tyr Glu Ser Lys Ser Asp His Arg Ser Val Gly Arg Ser Ser
            515                 520                 525

Arg Ala Thr Ser Ser Ser Asp Asn Ser Glu Thr Phe Val Gly Asn Ser
530                 535                 540
```

```
Ser Ser Asn His Ser Ala Leu His Ser Leu Val Ser Ser Leu Lys Gln
545                 550                 555                 560

Glu Met Thr Lys Gln Lys Ile Glu Tyr Glu Ser Arg Ile Lys Ser Leu
                565                 570                 575

Glu Gln Arg Asn Leu Thr Leu Glu Thr Glu Met Met Ser Leu His Asp
            580                 585                 590

Glu Leu Asp Gln Glu Arg Lys Lys Phe Thr Met Ile Glu Ile Lys Met
        595                 600                 605

Arg Asn Ala Glu Arg Ala Lys Glu Asp Ala Glu Lys Arg Asn Asp Met
    610                 615                 620

Leu Gln Lys Glu Met Glu Gln Phe Phe Ser Thr Phe Gly Glu Leu Thr
625                 630                 635                 640

Val Glu Pro Arg Arg Thr Glu Arg Gly Asn Thr Ile Trp Ile Gln
                645                 650                 655

<210> SEQ ID NO 12
<211> LENGTH: 2417
<212> TYPE: DNA
<213> ORGANISM: Homo sapiens

<400> SEQUENCE: 12
aaaacttaaa tatagctacc accgctttga aaggaatggt ttgtgtccaa acagcatttt      60
ccagacaagc tctgtacttt tttgccaaaa gaattaactt taaactgaag gcagtggaca     120
gttaaacaag agtcggcact gggaacagct gtgcgtagac cagaccagtg acttataagg     180
aggcgatcga gatcggatga cagcaaatca tgaaagctac ctcctcatgg caagcaccca     240
gaatgatatg gaagactggg tgaagtcaat ccgccgagtc atatgggac ctttcggagg      300 aggcatttt ggacagaaac tggaggatac tgttcgttat gagaagagat atgggaaccg      360
tctggctccg atgttggtgg agcagtgcgt ggactttatc cgacaaaggg ggctgaaaga     420
agagggtctc tttcgactgc caggccaggc taatcttgtt aaggagctcc aagatgcctt     480
tgactgtggg gagaagccat catttgacag caacacagat gtacacacgg tggcatcact     540
tcttaagctg tacctccgag aacttccaga accagttatt ccttatgcga agtatgaaga     600 tttttttgtca tgtgccaaac tgctcagcaa ggaagaggaa gcaggtgtta aggaattagc     660
aaagcaggtg aagagtttgc cagtggtaaa ttacaacctc ctcaagtata tttgcagatt     720
cttggatgaa gtacagtcct actcgggagt taacaaaatg agtgtgcaga acttggcaac     780
ggtctttggt cctaatatcc tgcgcccca agtggaagat cctttgacta tcatggaggg      840
cactgtggtg gtccagcagt tgatgtcagt gatgattagc aaacatgatt gcctctttcc     900
caaagatgca gaactacaaa gcaagcccca agatggagtg agcaacaaca atgaaattca     960
gaagaaagcc accatgggc agttacagaa caaggagaac aataacacca aggacagccc     1020
tagtaggcag tgctcctggg acaagtctga gtcaccccag agaagcagca tgaacaatgg     1080 atccccaca gctctatcag gcagcaaaac caacagccca agaacagtg ttcacaagct      1140 agatgtgtct agaagcccc ctctcatggt caaaagaaac ccagccttta taagggtag      1200 tgggatagtt accaatgggt ccttcagcag cagtaatgca gaaggtcttg agaaaaccca     1260
aaccaccccc aatgggagcc tacaggccag aaggagctct tcactgaagg tatctggtac     1320
caaaatgggc acgcacagtg tacagaatgg aacggtgcgc atgggcatt tgaacagcga     1380 cacactcggg aaccccacaa atgttcgaaa catgagctgg ctgccaaatg gctatgtgac     1440
cctgagggat aacaagcaga agaacaagc tggagagtta ggccagcaca acagactgtc     1500
```

-continued

| | |
|---|---|
| cacctatgat aatgtccatc aacagttctc catgatgaac cttgatgaca agcagagcat | 1560 |
| tgacagtgct acctggtcca cttcctcctg tgaaatctcc ctccctgaga actccaactc | 1620 |
| ctgtcgctct tctaccacca cctgcccaga gcaagacttt tttgggggga actttgagga | 1680 |
| ccctgttttg gatgggcccc cgcaggacga ccttttcccac cccagggact atgaaagcaa | 1740 |
| aagtgaccac aggagtgtgg gaggtcgaag tagtcgtgcc accagtagca gtgacaacag | 1800 |
| tgagacattt gtgggcaaca gcagcagcaa ccacagtgca ctgcacagtt tagtttccag | 1860 |
| cctgaaacag gaaatgacca aacagaagat agagtatgag tccaggataa agagcttaga | 1920 |
| acagcgaaac ttgactttgg aaacagaaat gatgagcctc catgatgaac tggatcagga | 1980 |
| gaggaaaaag ttcacaatga tagaaataaa aatgcgaaat gccgagcgag caaaagaaga | 2040 |
| tgccgagaaa agaaatgaca tgctacagaa agaagtggag cagtttttttt ccacgtttgg | 2100 |
| agaactgaca gttgaaccca ggagaaccga gagaggaaac acaatatgga ttcagtgagc | 2160 |
| ctgctttcgc ctgctgtctc tgatggctct ggcaaggact ccagggattc tggtgggata | 2220 |
| tgacttagaa ccaggtggct ggtcacctgg atgtacagaa gtctaactgg tgaaggaata | 2280 |
| tcatttacag acattaaaca tccatatctg caatgtgtac caaagttata tcatgcccca | 2340 |
| taatgctact gtcaagtgtt acaactggat atgtgtatat agagtagttt ttcaaaagta | 2400 |
| aactaaaaat gagaagc | 2417 |

<210> SEQ ID NO 13
<211> LENGTH: 653
<212> TYPE: PRT
<213> ORGANISM: Homo sapiens

<400> SEQUENCE: 13

```
Met Thr Ala Asn His Glu Ser Tyr Leu Leu Met Ala Ser Thr Gln Asn
1               5                   10                  15

Asp Met Glu Asp Trp Val Lys Ser Ile Arg Arg Val Ile Trp Gly Pro
            20                  25                  30

Phe Gly Gly Gly Ile Phe Gly Gln Lys Leu Glu Asp Thr Val Arg Tyr
        35                  40                  45

Glu Lys Arg Tyr Gly Asn Arg Leu Ala Pro Met Leu Val Glu Gln Cys
    50                  55                  60

Val Asp Phe Ile Arg Gln Arg Gly Leu Lys Glu Glu Gly Leu Phe Arg
65                  70                  75                  80

Leu Pro Gly Gln Ala Asn Leu Val Lys Glu Leu Gln Asp Ala Phe Asp
                85                  90                  95

Cys Gly Glu Lys Pro Ser Phe Asp Ser Asn Thr Asp Val His Thr Val
            100                 105                 110

Ala Ser Leu Leu Lys Leu Tyr Leu Arg Glu Leu Pro Glu Pro Val Ile
        115                 120                 125

Pro Tyr Ala Lys Tyr Glu Asp Phe Leu Ser Cys Ala Lys Leu Leu Ser
    130                 135                 140

Lys Glu Glu Glu Ala Gly Val Lys Glu Leu Ala Lys Gln Val Lys Ser
145                 150                 155                 160

Leu Pro Val Val Asn Tyr Asn Leu Leu Lys Tyr Ile Cys Arg Phe Leu
                165                 170                 175

Asp Glu Val Gln Ser Tyr Ser Gly Val Asn Lys Met Ser Val Gln Asn
            180                 185                 190

Leu Ala Thr Val Phe Gly Pro Asn Ile Leu Arg Pro Lys Val Glu Asp
        195                 200                 205
```

```
Pro Leu Thr Ile Met Glu Gly Thr Val Val Gln Gln Leu Met Ser
    210                 215                 220

Val Met Ile Ser Lys His Asp Cys Leu Phe Pro Lys Asp Ala Glu Leu
225                 230                 235                 240

Gln Ser Lys Pro Gln Asp Gly Val Ser Asn Asn Glu Ile Gln Lys
                245                 250                 255

Lys Ala Thr Met Gly Gln Leu Gln Asn Lys Glu Asn Asn Thr Lys
            260                 265                 270

Asp Ser Pro Ser Arg Gln Cys Ser Trp Asp Lys Ser Glu Ser Pro Gln
        275                 280                 285

Arg Ser Met Asn Asn Gly Ser Pro Thr Ala Leu Ser Gly Ser Lys
    290                 295                 300

Thr Asn Ser Pro Lys Asn Ser Val His Lys Leu Asp Val Ser Arg Ser
305                 310                 315                 320

Pro Pro Leu Met Val Lys Lys Asn Pro Ala Phe Asn Lys Gly Ser Gly
                325                 330                 335

Ile Val Thr Asn Gly Ser Phe Ser Ser Ser Asn Ala Glu Gly Leu Glu
            340                 345                 350

Lys Thr Gln Thr Thr Pro Asn Gly Ser Leu Gln Ala Arg Arg Ser Ser
        355                 360                 365

Ser Leu Lys Val Ser Gly Thr Lys Met Gly Thr His Ser Val Gln Asn
    370                 375                 380

Gly Thr Val Arg Met Gly Ile Leu Asn Ser Asp Thr Leu Gly Asn Pro
385                 390                 395                 400

Thr Asn Val Arg Asn Met Ser Trp Leu Pro Asn Gly Tyr Val Thr Leu
                405                 410                 415

Arg Asp Asn Lys Gln Lys Glu Gln Ala Gly Glu Leu Gly Gln His Asn
            420                 425                 430

Arg Leu Ser Thr Tyr Asp Asn Val His Gln Gln Phe Ser Met Met Asn
        435                 440                 445

Leu Asp Asp Lys Gln Ser Ile Asp Ser Ala Thr Trp Ser Thr Ser Ser
    450                 455                 460

Cys Glu Ile Ser Leu Pro Glu Asn Ser Asn Ser Cys Arg Ser Ser Thr
465                 470                 475                 480

Thr Thr Cys Pro Glu Gln Asp Phe Phe Gly Gly Asn Phe Glu Asp Pro
                485                 490                 495

Val Leu Asp Gly Pro Pro Gln Asp Asp Leu Ser His Pro Arg Asp Tyr
            500                 505                 510

Glu Ser Lys Ser Asp His Arg Ser Val Gly Gly Arg Ser Ser Arg Ala
        515                 520                 525

Thr Ser Ser Ser Asp Asn Ser Glu Thr Phe Val Gly Asn Ser Ser Ser
    530                 535                 540

Asn His Ser Ala Leu His Ser Leu Val Ser Ser Leu Lys Gln Glu Met
545                 550                 555                 560

Thr Lys Gln Lys Ile Glu Tyr Glu Ser Arg Ile Lys Ser Leu Glu Gln
                565                 570                 575

Arg Asn Leu Thr Leu Glu Thr Glu Met Met Ser Leu His Asp Glu Leu
            580                 585                 590

Asp Gln Glu Arg Lys Lys Phe Thr Met Ile Glu Ile Lys Met Arg Asn
        595                 600                 605

Ala Glu Arg Ala Lys Glu Asp Ala Glu Lys Arg Asn Asp Met Leu Gln
    610                 615                 620
```

Lys Glu Val Glu Gln Phe Phe Ser Thr Phe Gly Glu Leu Thr Val Glu
625                 630                 635                 640

Pro Arg Arg Thr Glu Arg Gly Asn Thr Ile Trp Ile Gln
            645                 650

<210> SEQ ID NO 14
<211> LENGTH: 1856
<212> TYPE: DNA
<213> ORGANISM: Homo sapiens

<400> SEQUENCE: 14

| | | | | | | |
|---|---|---|---|---|---|---|
| gcattttgg | acagaaactg | gaggatactg | ttcgttatga | aagagatat | gggaaccgtc | 60 |
| tggctccgat | gttggtggag | cagtgcgtgg | actttatccg | acaaagggg | ctgaaagaag | 120 |
| agggtctctt | tcgactgcca | ggccaggcta | atcttgttaa | ggagctccaa | gatgcctttg | 180 |
| actgtgggga | aagccatca | tttgacagca | acacagatgt | acacacggtg | gcatcacttc | 240 |
| ttaagctgta | cctccgagaa | cttccagaac | cagttattcc | ttatgcgaag | tatgaagatt | 300 |
| ttttgtcatg | tgccaaactg | ctcagcaagg | aagaggaagc | aggtgttaag | gaattagcaa | 360 |
| agcaggtgaa | gagtttgcca | gtggtaaatt | acaacctcct | caagtatatt | tgcagattct | 420 |
| tggatgaagt | acagtcctac | tcgggagtta | acaaaatgag | tgtgcagaac | ttggcaacgg | 480 |
| tctttggtcc | taatatcctg | cgccccaaag | tggaagatcc | tttgactatc | atggagggca | 540 |
| ctgtggtggt | ccagcagttg | atgtcagtga | tgattagcaa | acatgattgc | ctctttccca | 600 |
| aagatgcaga | actacaaagc | aagccccaag | atggagtgag | caacaacaat | gaaattcaga | 660 |
| agaaagccac | catggggcag | ttacagaaca | aggagaacaa | taacaccaag | gacagcccta | 720 |
| gtaggcagtg | ctcctgggac | aagtctgagt | caccccagag | aagcagcatg | aacaatggat | 780 |
| cccccacagc | tctatcaggc | agcaaaacca | acagcccaaa | gaacagtgtt | cacaagctag | 840 |
| atgtgtctag | aagccccccc | tcatggtca | aaaagaaccc | agcctttaat | aagggtagtg | 900 |
| ggatagttac | caatgggtcc | ttcagcagca | gtaatgcaga | aggtcttgag | aaaacccaaa | 960 |
| ccaccccccaa | tggagcctga | caggccagaa | ggagctcttc | actgaaggta | tctggtacca | 1020 |
| aaatgggcac | gcacagtgta | cagaatggaa | cggtgcgcat | gggcattttg | aacagcgaca | 1080 |
| cactcgggaa | cccacacaaat | gttcgaaaca | tgagctggct | gccaaatggc | tatgtgaccc | 1140 |
| tgagggataa | caagcagaaa | gaacaagctg | gagagttagg | ccagcacaac | agactgtcca | 1200 |
| cctatgataa | tgtccatcaa | cagttctcca | tgatgaacct | tgatgacaag | cagagcattg | 1260 |
| acagtgctac | ctggtccact | tcctcctgtg | aaatctccct | ccctgagaac | tccaactcct | 1320 |
| gtcgctcttc | taccaccacc | tgcccagagc | aagactttt | tgggggggaac | tttgaggacc | 1380 |
| ctgtttgga | tgggcccccg | caggacgacc | tttcccaccc | cagggactat | gaaagcaaaa | 1440 |
| gtgaccacag | gagtgtggga | ggtcgaagta | gtcgtgccac | cagtagcagt | gacaacagtg | 1500 |
| agacatttgt | gggcaacagc | agcagcaacc | acagtgcact | gcacagttta | gtttccagcc | 1560 |
| tgaaacagga | aatgaccaaa | cagaagatag | agtatgagtc | caggataaag | agcttagaac | 1620 |
| agcgaaactt | gactttggaa | acagaaatga | tgagcctcca | tgatgaactg | gatcaggaga | 1680 |
| ggaaaaagtt | cacaatgata | gaaataaaaa | tgcgaaatgc | cgagcgagca | aaagaagatg | 1740 |
| ccgagaaaag | aaatgacatg | ctacagaaag | aaatggagca | gttttttccc | acgtttggag | 1800 |
| aactgacagt | ggaacccagg | agaaccgaga | gggaaacac | aatatggatt | cagtga | 1856 |

<210> SEQ ID NO 15
<211> LENGTH: 618

<212> TYPE: PRT
<213> ORGANISM: Homo sapiens

<400> SEQUENCE: 15

```
Gly Ile Phe Gly Gln Lys Leu Glu Asp Thr Val Arg Tyr Glu Lys Arg
1               5                   10                  15

Tyr Gly Asn Arg Leu Ala Pro Met Leu Val Glu Gln Cys Val Asp Phe
            20                  25                  30

Ile Arg Gln Arg Gly Leu Lys Glu Glu Gly Leu Phe Arg Leu Pro Gly
        35                  40                  45

Gln Ala Asn Leu Val Lys Glu Leu Gln Asp Ala Phe Asp Cys Gly Glu
    50                  55                  60

Lys Pro Ser Phe Asp Ser Asn Thr Asp Val His Thr Val Ala Ser Leu
65                  70                  75                  80

Leu Lys Leu Tyr Leu Arg Glu Leu Pro Glu Pro Val Ile Pro Tyr Ala
                85                  90                  95

Lys Tyr Glu Asp Phe Leu Ser Cys Ala Lys Leu Leu Ser Lys Glu Glu
            100                 105                 110

Glu Ala Gly Val Lys Glu Leu Ala Lys Gln Val Lys Ser Leu Pro Val
        115                 120                 125

Val Asn Tyr Asn Leu Leu Lys Tyr Ile Cys Arg Phe Leu Asp Glu Val
    130                 135                 140

Gln Ser Tyr Ser Gly Val Asn Lys Met Ser Val Gln Asn Leu Ala Thr
145                 150                 155                 160

Val Phe Gly Pro Asn Ile Leu Arg Pro Lys Val Glu Asp Pro Leu Thr
                165                 170                 175

Ile Met Glu Gly Thr Val Val Gln Gln Leu Met Ser Val Met Ile
            180                 185                 190

Ser Lys His Asp Cys Leu Phe Pro Lys Asp Ala Glu Leu Gln Ser Lys
        195                 200                 205

Pro Gln Asp Gly Val Ser Asn Asn Glu Ile Gln Lys Lys Ala Thr
    210                 215                 220

Met Gly Gln Leu Gln Asn Lys Glu Asn Asn Thr Lys Asp Ser Pro
225                 230                 235                 240

Ser Arg Gln Cys Ser Trp Asp Lys Ser Glu Ser Pro Gln Arg Ser Ser
            245                 250                 255

Met Asn Asn Gly Ser Pro Thr Ala Leu Ser Gly Ser Lys Thr Asn Ser
        260                 265                 270

Pro Lys Asn Ser Val His Lys Leu Asp Val Ser Arg Ser Pro Pro Leu
    275                 280                 285

Met Val Lys Lys Asn Pro Ala Phe Asn Lys Gly Ser Gly Ile Val Thr
290                 295                 300

Asn Gly Ser Phe Ser Ser Ser Asn Ala Glu Gly Leu Glu Lys Thr Gln
305                 310                 315                 320

Thr Thr Pro Asn Gly Ser Leu Gln Ala Arg Arg Ser Ser Ser Leu Lys
                325                 330                 335

Val Ser Gly Thr Lys Met Gly Thr His Ser Val Gln Asn Gly Thr Val
            340                 345                 350

Arg Met Gly Ile Leu Asn Ser Asp Thr Leu Gly Asn Pro Thr Asn Val
        355                 360                 365

Arg Asn Met Ser Trp Leu Pro Asn Gly Tyr Val Thr Leu Arg Asp Asn
    370                 375                 380

Lys Gln Lys Glu Gln Ala Gly Glu Leu Gly Gln His Asn Arg Leu Ser
385                 390                 395                 400
```

```
Thr Tyr Asp Asn Val His Gln Gln Phe Ser Met Met Asn Leu Asp Asp
                405                 410                 415
Lys Gln Ser Ile Asp Ser Ala Thr Trp Ser Thr Ser Cys Glu Ile
            420                 425                 430
Ser Leu Pro Glu Asn Ser Asn Ser Cys Arg Ser Ser Thr Thr Thr Cys
        435                 440                 445
Pro Glu Gln Asp Phe Phe Gly Gly Asn Phe Glu Asp Pro Val Leu Asp
    450                 455                 460
Gly Pro Pro Gln Asp Asp Leu Ser His Pro Arg Asp Tyr Glu Ser Lys
465                 470                 475                 480
Ser Asp His Arg Ser Val Gly Gly Arg Ser Ser Arg Ala Thr Ser Ser
                485                 490                 495
Ser Asp Asn Ser Glu Thr Phe Val Gly Asn Ser Ser Ser Asn His Ser
            500                 505                 510
Ala Leu His Ser Leu Val Ser Ser Leu Lys Gln Glu Met Thr Lys Gln
        515                 520                 525
Lys Ile Glu Tyr Glu Ser Arg Ile Lys Ser Leu Glu Gln Arg Asn Leu
    530                 535                 540
Thr Leu Glu Thr Glu Met Met Ser Leu His Asp Glu Leu Asp Gln Glu
545                 550                 555                 560
Arg Lys Lys Phe Thr Met Ile Glu Ile Lys Met Arg Asn Ala Glu Arg
                565                 570                 575
Ala Lys Glu Asp Ala Glu Lys Arg Asn Asp Met Leu Gln Lys Glu Met
            580                 585                 590
Glu Gln Phe Phe Ser Thr Phe Gly Glu Leu Thr Val Glu Pro Arg Arg
        595                 600                 605
Thr Glu Arg Gly Asn Thr Ile Trp Ile Gln
    610                 615

<210> SEQ ID NO 16
<211> LENGTH: 531
<212> TYPE: DNA
<213> ORGANISM: Homo sapiens

<400> SEQUENCE: 16
ccgtctggct ccgatgttgg tggagcagtg cgtggacttt atccgacaaa gggggctgaa      60
agaagagggt ctctttcgac tgccaggcca ggctaatctt gttaaggagc tccaagatgc     120
ctttgactgt ggggagaagc catcatttga cagcaacaca gatgtacaca cggtggcatc     180
acttcttaag ctgtacctcc gagaacttcc agaaccagtt attccttatg cgaagtatga     240
agatttttg tcatgtgcca aactgctcag caaggaagag gaagcaggtg ttaaggaatt     300
agcaaagcag gtgaagagtt tgccagtggt aaattacaac ctcctcaagt atatttgcag     360
attcttggat gaagtacagt cctactcggg agttaacaaa atgagtgtgc agaacttggc     420
aacggtcttt ggtcctaata tcctgcgccc caaagtggaa gatcctttga ctatcatgga     480
gggcactgtg gtggtccagc agttgatgtc agtgatgatt agcaaacatg a              531

<210> SEQ ID NO 17
<211> LENGTH: 177
<212> TYPE: PRT
<213> ORGANISM: Homo sapiens

<400> SEQUENCE: 17

Arg Leu Ala Pro Met Leu Val Glu Gln Cys Val Asp Phe Ile Arg Gln
1               5                   10                  15
```

```
Arg Gly Leu Lys Glu Glu Gly Leu Phe Arg Leu Pro Gly Gln Ala Asn
            20                  25                  30
Leu Val Lys Glu Leu Gln Asp Ala Phe Asp Cys Gly Glu Lys Pro Ser
            35                  40                  45
Phe Asp Ser Asn Thr Asp Val His Thr Val Ala Ser Leu Leu Lys Leu
 50                  55                  60
Tyr Leu Arg Glu Leu Pro Glu Pro Val Ile Pro Tyr Ala Lys Tyr Glu
 65                  70                  75                  80
Asp Phe Leu Ser Cys Ala Lys Leu Leu Ser Lys Glu Glu Glu Ala Gly
                85                  90                  95
Val Lys Glu Leu Ala Lys Gln Val Lys Ser Leu Pro Val Val Asn Tyr
            100                 105                 110
Asn Leu Leu Lys Tyr Ile Cys Arg Phe Leu Asp Glu Val Gln Ser Tyr
            115                 120                 125
Ser Gly Val Asn Lys Met Ser Val Gln Asn Leu Ala Thr Val Phe Gly
        130                 135                 140
Pro Asn Ile Leu Arg Pro Lys Val Glu Asp Pro Leu Thr Ile Met Glu
145                 150                 155                 160
Gly Thr Val Val Val Gln Gln Leu Met Ser Val Met Ile Ser Lys His
                    165                 170                 175
Asp

<210> SEQ ID NO 18
<211> LENGTH: 19
<212> TYPE: DNA
<213> ORGANISM: Artificial Sequence
<220> FEATURE:
<223> OTHER INFORMATION: Artificially synthesized siRNA molecule

<400> SEQUENCE: 18
aggcatcagc ggacctcat                                                  19
```

COMPOSITIONS AND METHODS FOR ANGIOGENESIS-RELATED MOLECULES AND TREATMENTS

TECHNICAL FIELD

The present invention relates to isolated nucleic acid molecules and their encoded polypeptides that are involved in the process of angiogenesis. In view of their involvement in angiogenesis, the invention is also concerned with the therapy of angiogenesis-related disorders, the screening of compounds for pro- and anti-angiogenic activity, and the diagnosis and prognosis of angiogenesis-related disorders. The invention is also concerned with siRNA molecules targeted to the nucleic acid molecules of the invention and their use for therapeutic application in the treatment of angiogenesis-related disorders.

BACKGROUND ART

It will be clearly understood that, although a number of prior art publications are referred to herein to describe background information, this reference does not constitute an admission that any of these documents forms part of the common general knowledge in the art, in Australia or in any other country. The discussion of the references states what their authors assert, and the applicants reserve the right to challenge the accuracy and pertinency of the cited documents.

Angiogenesis, the formation of new blood vessels from pre-existing vessels, plays a critical role in many physiological and pathologic processes including embryogenesis, wound healing, tumour growth and metastasis (Augustin, 1998; Hanahan, 1997). Thus, the angiogenic process is considered an excellent target for therapeutic intervention. Identification of key regulatory molecules has principally used in vitro models in which endothelial cells (EC) are cultured on extracellular matrix (ECM) components such as collagen, fibrinogen or fibronectin, with identification of targets that are involved in events such as migration or proliferation which are elements of angiogenesis but are not specific for it. However, one problem in these investigations is the fact that the assays are generally performed on a flat or two dimensional (2D) environment, whereas EC morphogenesis to form capillary tubes requires a 3D matrix, allowing the establishment of important polarity cues. The use of such 3D assays, which include matrices of collagen type 1, fibrin, or Matrigel, recapitulates many of the events in angiogenesis, and has allowed dissection of the cellular and molecular events in angiogenesis (Gamble et al., 1993; 1999; Bayless and Davis, 2002; Meyer et al., 1997). Data using these assays to define genes altered during angiogenesis has supported the ideas firstly that there are fundamental differences between cells responding on 3D versus 2D matrices, and secondly that genes specific for angiogenesis might exist.

The mammalian Rho family of small GTPases has been implicated in diverse cellular functions, including reorganisation of the actin cytoskeleton, cell growth control, transcription regulation and membrane trafficking (Van Aelst and D'Souza-Schorey, 1997). The Rho family of small GTPases consists of at least 20 members: Rho (A,B,C), Rac (1,2,3), Cdc42, TC10, TCL, Chp (1,2), RhoG, Rnd (1,2,3), RhoBTB (1,2), RhoD, Rif and TTF (Etienne-Manneville and Hall, 2002). Like other members of the Ras superfamily, Rho proteins act as molecular switches to control cellular processes by cycling between active GTP-bound and inactive GDP-bound states. Regulation of these GTPases occurs via three major classes of regulatory proteins. The guanine nucleotide exchange factors (GEF) regulate activation through GDP-GTP exchange, GTPase-activating proteins (GAPs), which promote hydrolysis of the GTP to GDP-bound form, since the Rho proteins themselves display little if any basal GTPase activity and guanine nucleotide dissociation inhibitors (GDIs) which stabilise the inactive GDP-bound form of the protein (Mackay and Hall, 1998). At least 134 of these regulatory proteins have now been defined (Etienne-Manneville and Hall, 2002).

The function of the Rho family in endothelial morphogenesis is only now being elucidated, and it appears that different Rho family members play specific roles. Rho and Rac are important for regulation of permeability and cell migration (Wojciak-Stothard et al., 2001; Nobes and Hall, 1999). Rho is also important for EC attachment and apoptosis (Chrzanowska-Wodnicka and Burridge, 1996; Hippenstiel et al., 2002), while Cdc42 and Racl are implicated in vacuole and subsequent lumen formation (Bayless and Davis, 2002). Given the limited number of RhoGTPases and the seeming over-abundance of RhoGAPs, it is likely that the RhoGAPs may partly provide the specificity in control of function of the RhoGTPases.

SUMMARY OF THE INVENTION

A novel RhoGAP called BNO69 which is essential for angiogenesis has now been cloned and characterised as described in our co-pending International Application No. PCT/AU02/01282 the contents of which are incorporated herein by reference, and novel therapies for inhibition of BNO69 have been devised.

Therapies which inhibit the expanding vasculature are desirable for the treatment of angiogenesis-related disorders which result in uncontrolled or enhanced angiogenesis, or a disorder in which a decreased vasculature is of benefit. These include, but are not limited to, cancer; inflammatory disorders including arthritis; corneal, retinal or choroidal neovascularization including macular degeneration and diabetic retinopathy; psoriasis; cardiovascular diseases.

In the present instance this involves reduction of the expression and activity of the BNO69 gene product.

Inhibiting the function of a gene or protein can be achieved in a variety of ways. Antisense nucleic acid methodologies generally represent one approach to inactivation of genes whose altered expression is causative of a disorder. In particular, RNA interference using short interfering RNA (siRNA) molecules. As will be understood by the person skilled in the art, an siRNA is a short sequence of RNA which is the complement of a segment of a transcribed RNA and consequently binds thereto, and, in so doing, modulates or silences expression of the gene in question.

Accordingly, in a first aspect of the invention there is provided a short interfering RNA (siRNA) molecule comprising a complement of a segment of the mRNA transcribed from the BNO69 gene, wherein said siRNA molecule modulates the expression of BNO69 by RNA interference. Such modulation may include partial or complete silencing of the BNO69 gene. The siRNA may be specific for any one or more splicing isoforms of the BNO69 gene, or for a mutant thereof.

As will be appreciated by the person skilled in the art, a siRNA molecule used to modulate or silence the expression of BNO69 may be in the form of single-stranded antisense, double-stranded antisense or double-stranded antisense with chemical modifications.

In one embodiment of the invention, the siRNA molecule comprises the complement of the following segments of the BNO69 gene:

```
5'-GTAGTCGTGCCACCAGTAG-3'        (SEQ ID NO: 1)

5'-AGACTTGGCATACTCGCTG-3'        (SEQ ID NO: 2)
```

The invention therefore provides a nucleic acid molecule comprising the sequence set forth in one of SEQ ID NOs: 1 or 2.

In a still further embodiment, the siRNA molecule comprises either of the following sequences:

```
5'-GUAGUCGUGCCACCAGUAG-3'        (SEQ ID NO: 3)

5'-AGACUUGGCAUACUCGCUG-3'        (SEQ ID NO: 4)
```

In a further embodiment, a siRNA molecule of the invention is incorporated into a short hairpin RNA (shRNA) molecule. In a preferred embodiment, the shRNA molecule comprises a nucleotide sequence corresponding to the siRNA molecule, followed by a generic nucleotide linker sequence, typically a 9 nucleotide sequence (advantageously with the sequence TTCAAGAGA as represented by SEQ ID NO: 5), followed by the reverse complement of the nucleotide sequence corresponding to the siRNA molecule. Upon integration in the host cell genome the nucleotide sequence corresponding to the siRNA molecule forms a double stranded structure by annealing to its reverse complement. The generic sequence forms a loop at one end of the double stranded molecule.

In an embodiment the shRNA has either of the following sequences:

```
                                                  (SEQ ID NO: 6)
5'-GATCCCCGTAGTCGTGCCACCAGTAGTTCAAGAGACTACTGGTGGCA

CGACTACTTTTTGGAAA-3'

(SEQ ID NO: 7)
5'-GATCCCCAGACTTGGCATACTCGCTGTTCAAGAGCAGCGAGTATGCC

AAGTCTTTTTTGGAAA-3'
```

The siRNA, shRNA molecules or nucleic acid molecules of the present invention may be used to modulate the expression of BNO69, or may be administered to a subject to treat or prevent an angiogenesis-related disorder, or a disorder in which a decreased vasculature is of benefit.

Accordingly in a further aspect of the invention there is provided a method of modulating the expression of BNO69, or a splicing isoform, or mutant thereof, comprising administering to a subject one or more of a siRNA molecule comprising a complement of a segment of the mRNA transcribed from BNO69, a shRNA molecule targeted to BNO69, or a nucleic acid molecule as described above.

In a further aspect there is provided a method of treating an angiogenesis-related disorder, or a disorder in which a decreased vasculature is of benefit, comprising administering one or more of a siRNA molecule comprising a complement of a segment of the mRNA transcribed from BNO69, a shRNA molecule targeted to BNO69, or a nucleic acid molecule as described above, to a subject.

In a further aspect of the invention there is provided the use of one or more of a siRNA molecule comprising a complement of a segment of the mRNA transcribed from BNO69, a shRNA molecule targeted to BNO69, or a nucleic acid molecule as described above, in the manufacture of a medicament for the treatment of an angiogenesis-related disorder, or a disorder in which a decreased vasculature is of benefit.

The siRNA molecules, shRNA molecules, or nucleic acid molecules of the invention may be cloned into a vector which may be used to modulate the expression of BNO69, or a splicing isoform, or mutant thereof, or may be administered to a subject to treat or prevent an angiogenesis-related disorder including but not limited to those described above.

Vector systems may be plasmid, cosmid or viral in origin, as would be appreciated by the person skilled in the art. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See for example Goldman et al., 1997).

In a further aspect, the present invention provides a method of modulating the expression of BNO69, or a splicing isoform, or mutant thereof, comprising administering to a subject a vector comprising either a siRNA molecule, shRNA molecule, or nucleic acid molecule of the invention.

In a further aspect there is provided a method of treating an angiogenesis-related disorder, or a disorder in which a decreased vasculature is of benefit, comprising administering a vector comprising either a siRNA molecule, shRNA molecule, or nucleic acid molecule of the invention, to a subject.

In a further aspect of the invention there is provided the use of a vector comprising a siRNA molecule, a shRNA, or a nucleic acid molecule of the invention in the manufacture of a medicament for the treatment of an angiogenesis-related disorder, or a disorder in which a decreased vasculature is of benefit.

Any of the siRNA molecules, shRNA molecules, nucleic acid molecules, or vectors comprising such molecules form a part of the present invention, as do pharmaceutical compositions containing these and a pharmaceutically acceptable carrier.

Any of the therapeutic methods described above may be applied to any subject, including, for example, a mammal. The mammal may be a human, or may be a domestic, companion or zoo animal. While it is particularly contemplated that the pharmaceutical compositions of the invention are suitable for use in medical treatment of humans, they are also applicable to veterinary treatment, including treatment of companion animals such as dogs and cats, and domestic animals such as horses, cattle and sheep, or zoo animals such as non-human primates, felids, canids, bovids, and ungulates.

Isoforms of the BNO69 gene have been identified. The siRNA or shRNA molecules of the invention may be targeted to any one or more of these isoforms. Specifically, any one or more of isoform I, II or III may be targeted. The nucleotide and amino acid sequence of isoform I is represented by SEQ ID Numbers: 8 and 9 respectively. Isoform II is the molecule identified as BNO69 in PCT/AU02/01282 and its nucleotide and amino acid sequences are represented by SEQ ID Numbers: 10 and 11 respectively. The nucleotide and amino acid sequence of isoform III is represented by SEQ ID Numbers: 12 and 13 respectively. The BNO69 isoforms share a common region of sequence identity, the nucleotide and amino acid sequence of which is represented by SEQ ID Numbers: 14 and 15 respectively. This region of identity includes a GAP domain, the nucleotide and amino acid sequence of which is represented by SEQ ID NO: 16 and 17 respectively. The siRNA or shRNA molecules of the invention may target the common region shared by all isoforms of BNO69, including the GAP domain, or may bind specifically to one isoform alone.

In a further aspect of the present invention, there is provided an isolated nucleic acid molecule comprising the sequence set forth in one of SEQ ID Numbers: 8, 12, 14 or 16.

Still further, there is provided an isolated nucleic acid molecule comprising the sequence set forth in one of SEQ ID Numbers: 8, 12, 14 or 16, or a fragment thereof, and which encodes a polypeptide that plays a role in an angiogenic process. Such a process may include, but is not restricted to, embryogenesis, the menstrual cycle, wound repair, tumour angiogenesis and exercise-induced muscle hypertrophy.

In addition, the present invention provides isolated nucleic acid molecules comprising the sequence set forth in one of SEQ ID Numbers: 8, 12, 14 or 16, or fragments thereof, that play a role in diseases associated with the angiogenic process. Such diseases include, but are not restricted to, cancer; inflammatory disorders including arthritis; corneal, retinal or choroidal neovascularization including macular degeneration and diabetic retinopathy; psoriasis; cardiovascular diseases. Useful fragments may include those which are unique and which do not overlap any previously identified genes, unique fragments which do overlap with a known sequence, and fragments which span alternative splice junctions etc.

The invention also encompasses an isolated nucleic acid molecule that is at least 70% identical to any one of SEQ ID Numbers: 8, 12, 14 or 16 and which encodes a polypeptide that plays a role in an angiogenic process. Such variants will have preferably at least about 85%, and most preferably at least about 95% sequence identity to these sequences.

Sequence identity is typically calculated using the BLAST algorithm, described in Altschul et al (1997) with the BLOSUM62 default matrix.

The invention also encompasses an isolated nucleic acid molecule which hybridizes under stringent conditions with any one of SEQ ID Numbers: 8, 12, 14 or 16, and which plays a role in an angiogenic process.

Hybridization with PCR probes is contemplated. The specificity of the probe, whether it is made from a highly specific region, e.g., the 5' regulatory region, or from a less specific region, e.g., a conserved motif such as the GAP domain, and the stringency of the hybridization or amplification will determine whether the probe identifies only naturally occurring sequences, allelic variants, or related sequences.

Probes used for the detection of related sequences, should preferably have at least 50% sequence identity to any of SEQ ID Numbers: 8, 12, 14 or 16. The hybridization probes of the present invention may be DNA or RNA.

Means for producing specific hybridization probes for any of SEQ ID Numbers: 8, 12, 14 or 16 include the cloning of these sequences into vectors for the production of mRNA probes. Such vectors are known in the art, and are commercially available. Hybridization probes may be labelled by radionuclides such as $^{32}P$ or $^{35}S$, or by enzymatic labels, such as alkaline phosphatase coupled to the probe via avidin/biotin coupling systems, or other methods known in the art.

Under stringent conditions, hybridization with $^{32}P$ labelled probes will most preferably occur at 42° C. in 750 mM NaCl, 75 mM trisodium citrate, 2% SDS, 50% formamide, 1× Denhart's, 10% (w/v) dextran sulphate and 100 µg/ml denatured salmon sperm DNA. Useful variations on these conditions will be readily apparent to those skilled in the art. The washing steps which follow hybridization most preferably occur at 65° C. in 15 mM NaCl, 1.5 mM trisodium citrate, and 1% SDS. Additional variations on these conditions will be readily apparent to those skilled in the art.

The nucleic acid molecules, or fragments thereof, of the present invention have a nucleotide sequence obtainable from a natural source. They therefore include naturally occurring normal, naturally occurring mutant, naturally occurring polymorphic alleles, differentially spliced transcripts, splice variants etc. Natural sources include animal cells and tissues, body fluids, tissue culture cells etc.

The nucleic acid molecules of the present invention can also be engineered using methods accepted in the art so as to alter the gene-encoding sequences for a variety of purposes. These include, but are not limited to, modification of the cloning, processing, and/or expression of the gene product. PCR reassembly of gene fragments and the use of synthetic oligonucleotides allow the engineering of the nucleic acid molecules of the present invention. For example, oligonucleotide-mediated site-directed mutagenesis can introduce mutations that create new restriction sites, alter glycosylation patterns and produce splice variants etc.

As a result of the degeneracy of the genetic code, a number of nucleic acid sequences representing the nucleic acid molecules of the present invention, some that may have minimal similarity to the naturally occurring sequence, may be produced. Thus, the invention includes each and every possible variation of polynucleotide sequence that could be made by selecting combinations based on possible codon choices. These combinations are made in accordance with the standard triplet genetic code as applied to the polynucleotide sequence of the naturally nucleic acid molecule, and all such variations are to be considered as being specifically disclosed.

The nucleic acid molecules of this invention are typically DNA molecules, and include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences that represent the nucleic acid molecules of the present invention, which possess a substantially different codon usage than that of the naturally occurring molecule. For example, codons may be selected to increase the rate of expression of the encoded peptide in a particular prokaryotic or eukaryotic host corresponding with the frequency that the host utilizes particular codons. Other reasons to alter the nucleotide sequence without altering the encoded amino acid sequence include the production of RNA transcripts having more desirable properties, such as a greater half-life, than transcripts produced from the naturally occurring molecule.

The invention also encompasses production of the nucleic acid molecules of the invention, entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of the nucleotide sequence. In cases where the complete coding sequence including its initiation codon and upstream regulatory sequences are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

The present invention allows for the preparation of purified polypeptides or proteins. In order to do this, host cells may be transfected with a nucleic acid molecule as described above. Typically, said host cells are transfected with an expression vector comprising a nucleic acid molecule according to the invention. A variety of expression vector/host systems may be utilized to contain and express the sequences. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express a polypeptide that is encoded by a nucleic acid molecule of the invention using various expression vectors including plasmid, cosmid and viral systems such as a vaccinia virus expression system. The invention is not limited by the host cell or vector employed.

The nucleic acid molecules, or variants thereof, of the present invention can be stably expressed in cell lines to allow long term production of recombinant proteins in mammalian systems. The nucleic acid sequences of the invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode a protein may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

According to still another aspect of the present invention there is provided an expression vector comprising a nucleic acid molecule of the invention as described above.

According to still another aspect of the present invention there is provided a cell comprising a nucleic acid molecule of the invention as described above. Preferably, said cell is an eukaryotic cell.

When large quantities of protein are needed such as for antibody production, vectors which direct high levels of expression may be used such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate polynucleotide sequences of the present invention are inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence and the relevant protein can subsequently be obtained by enzymatic cleavage of the fusion protein.

Fragments of polypeptides of the present invention may also be produced by direct peptide synthesis using solid-phase techniques. Automated synthesis may be achieved by using the ABI 431A Peptide Synthesizer (Perkin-Elmer). Various fragments of polypeptide may be synthesized separately and then combined to produce the full length molecule.

In a further aspect of the present invention there is provided an isolated polypeptide comprising the sequence set forth in one of SEQ ID Numbers: 9, 13, 15 or 17.

The present invention also provides an isolated polypeptide, or fragment thereof, comprising the sequence set forth in one of SEQ ID Numbers: 9, 13, 15 or 17 that plays a role in an angiogenic process. Such a process may include, but is not restricted to, embryogenesis, menstrual cycle, wound repair, tumour angiogenesis and exercise induced muscle hypertrophy.

In addition, the present invention provides an isolated polypeptide set forth in one of SEQ ID Numbers: 9, 13, 15 or 17, or fragments thereof, that plays a role in diseases associated with the angiogenic process. Diseases may include, but are not restricted to, cancer; inflammatory disorders including arthritis; corneal, retinal or choroidal neovascularization including macular degeneration and diabetic retinopathy; psoriasis; cardiovascular diseases.

The invention also encompasses an isolated polypeptide having at least 70%, preferably 85%, and more preferably 95%, identity to any one of SEQ ID Numbers: 9, 13, 15 or 17, and which plays a role in an angiogenic process.

Sequence identity is typically calculated using the BLAST algorithm, described in Altschul et al (1997) with the BLOSUM62 default matrix.

In a further aspect of the invention there is provided a method of preparing a polypeptide as described above, comprising the steps of:
(a) culturing cells as described above under conditions effective for production of the polypeptide; and
(b) harvesting the polypeptide.

According to still another aspect of the invention there is provided a polypeptide which is the product of the process described above.

Substantially purified protein or fragments thereof can be used in further biochemical analyses to establish secondary and tertiary structure. Such methodology is known in the art and includes, but is not restricted to, X-ray crystallography of crystals of the proteins or by nuclear magnetic resonance (NMR). Determination of structure allows for the rational design of pharmaceuticals to interact with the protein, alter protein charge configuration or charge interaction with other proteins, or to alter its function in the cell.

The invention has provided isoforms of BNO69, a gene involved in angiogenesis, and therefore enables methods for the modulation of angiogenesis.

As angiogenesis is critical in a number of pathological processes, the invention therefore also provides therapeutic methods for the treatment of angiogenesis-related disorders, and provides the diagnosis or prognosis of angiogenesis-related disorders associated with abnormalities in expression and/or function of BNO69.

Examples of such disorders include, but are not limited to, cancer; inflammatory disorders including arthritis; corneal, retinal or choroidal neovascularization including macular degeneration and diabetic retinopathy; psoriasis; cardiovascular diseases.

Therapeutic Applications

According to another aspect of the present invention there is provided a method of treating an angiogenesis-related disorder as described above, comprising modulating the expression or activity of a polypeptide of the invention.

In a further aspect, the invention provides a method of treating an angiogenesis-related disorder as described above, comprising administering a selective antagonist or agonist of a nucleic acid molecule or polypeptide of the invention to a subject.

In still another aspect of the invention there is provided the use of a selective antagonist or agonist of a nucleic acid molecule or polypeptide of the invention in the manufacture of a medicament for the treatment of an angiogenesis-related disorder as described above.

For the treatment of angiogenesis-related disorders which result in uncontrolled or enhanced angiogenesis, including but not limited to, cancer; inflammatory disorders including arthritis; corneal, retinal or choroidal neovascularization including macular degeneration and diabetic retinopathy; psoriasis; cardiovascular diseases, therapies which inhibit the expanding vasculature are desirable. This would involve inhibition of the nucleic acid molecules or polypeptides of the invention.

For the treatment of angiogenesis-related disorders which are characterised by inhibited or decreased angiogenesis, including but not limited to, ischaemic limb disease and coronary artery disease, therapies which enhance or promote vascular expansion are desirable. This would involve enhancement, stimulation or re-activation of the nucleic acid molecules or polypeptides of the invention.

Inhibiting Gene or Protein Function

Inhibiting the function of a gene or protein can be achieved in a variety of ways. As mentioned above, antisense nucleic acid methodologies represent one approach to inactivate genes that are causative of a disorder. Antisense or gene-targeted silencing strategies may include, but are not limited to, the use of antisense oligonucleotides, injection of antisense RNA, transfection of antisense RNA expression vectors, and the use of RNA interference (RNAi) or short interfering RNA (siRNA) as described above. Still further, catalytic nucleic acid molecules such as DNAzymes and ribozymes may be used for gene silencing (Breaker and Joyce, 1994; Haseloff and Gerlach, 1988). These molecules function by cleaving their target mRNA molecule rather than merely binding to it as in traditional antisense approaches.

In one aspect of the invention an isolated nucleic acid molecule, which is the complement of any one of the nucleic acid molecules described above may be administered to a subject. Typically, a complement is administered to a subject to treat or prevent an angiogenesis-related disorder. In a further aspect the complement is an RNA molecule that hybridizes with the mRNA encoded by a nucleic acid molecule of the invention, a short interfering RNA (siRNA) that hybridizes with the mRNA encoded by a nucleic acid molecule of the invention, or a catalytic nucleic acid molecule that is targeted to a nucleic acid molecule of the invention.

In a further aspect of the invention there is provided the use of an isolated nucleic acid molecule which is the complement of a nucleic acid molecule of the invention and which encodes an RNA molecule or a short interfering RNA (siRNA) that hybridizes with the mRNA encoded by a nucleic acid molecule of the invention, in the manufacture of a medicament for the treatment of an angiogenesis-related disorder.

Typically, a vector expressing the complement may be administered to a subject to treat or prevent an angiogenesis-related disorder including, but not limited to, those described above. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

In a further aspect purified protein according to the invention may be used to produce antibodies which specifically bind to a polypeptide of the invention. These antibodies may be used directly as an antagonist or indirectly as a targeting or delivery mechanism for bringing a pharmaceutical agent (such as a cytotoxic agent) to cells or tissues that express the polypeptide. Such antibodies may include, but are not limited to, polyclonal, monoclonal, chimeric and single chain antibodies as would be understood by the person skilled in the art.

For the production of antibodies, various hosts including rabbits, rats, goats, mice, humans, and others may be immunized by injection with a polypeptide of the invention or with any fragment or oligopeptide thereof, which has immunogenic properties. Various adjuvants may be used to increase immunological response, and include, but are not limited to, Freund's adjuvant, mineral gels such as aluminium hydroxide, and surface-active substances such as lysolecithin. Adjuvants used in humans include BCG (bacillus Calmette-Guerin) and *Corynebacterium parvum*.

It is preferred that the oligopeptides, peptides, or fragments used to induce antibodies to a polypeptide have an amino acid sequence consisting of at least about 5 amino acids, and, more preferably, of at least about 10 amino acids. It is also preferable that these oligopeptides, peptides, or fragments are identical to a portion of the amino acid sequence of the polypeptide and contain the entire amino acid sequence of a small, naturally occurring molecule. Short stretches of amino acids from these proteins may be fused with those of another protein, such as KLH, and antibodies to the chimeric molecule may be produced.

Monoclonal antibodies to a polypeptide of the invention may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler and Milstein, 1975; Kozbor et al., 1985; Cote et al., 1983; Cole et al., 1984).

Monoclonal antibodies produced may include, but are not limited to, mouse-derived antibodies, humanised antibodies and fully-human antibodies. For example, antibodies are obtained from transgenic mice that have been engineered to produce specific human antibodies in response to antigenic challenge. In one example of this technique, elements of the human heavy and light chain loci are introduced into strains of mice derived from embryonic stem cell lines that contain targeted disruptions of the endogenous heavy and light chain loci. These transgenic mice can synthesise human antibodies specific for human antigens and can be used to produce human antibody-secreting hybridomas. Methods for obtaining human antibodies from transgenic mice are described for example in Lonberg et al., 1994; Green et al., 1994; Taylor et al., 1994.

Antibodies may also be produced by inducing in vivo production in the lymphocyte population or by screening immunoglobulin libraries or panels of highly specific binding reagents as disclosed in the literature. (For example, see Orlandi et al., 1989; Winter et al., 1991).

Antibody fragments which contain specific binding sites for a polypeptide of the invention may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a protein and its specific antibody. A two-site, monoclonal-based immunoassay utilizing monoclonal antibodies reactive to two non-interfering epitopes is preferred, but a competitive binding assay may also be employed.

In a further aspect, antagonists may include peptides, phosphopeptides or small organic or inorganic compounds. These antagonists should disrupt the function of a nucleic acid molecule or polypeptide of the invention so as to provide the necessary therapeutic effect.

Peptides, phosphopeptides or small organic or inorganic compounds suitable for therapeutic applications may be identified using nucleic acid molecules and polypeptides of the invention in drug screening applications as described below.

Enhancing Gene or Protein Function

Enhancing, stimulating or re-activating a gene's or protein's function can be achieved in a variety of ways. In one aspect of the invention administration of an isolated nucleic acid molecule, as described above, to a subject may be initiated. Typically, a nucleic acid molecule of the invention can be administered to a subject to treat or prevent an angiogenesis-related disorder.

In a further aspect, there is provided the use of an isolated nucleic acid molecule, as described above, in the manufacture of a medicament for the treatment of an angiogenesis-related disorder.

Typically, a vector capable of expressing a polypeptide of the invention, or a fragment or derivative thereof, may be administered to a subject to treat or prevent a disorder including, but not limited to, those described above. Transducing retroviral vectors are often used for somatic cell gene therapy because of their high efficiency of infection and stable integration and expression. A nucleic acid molecule of the invention, or portions thereof, can be cloned into a retroviral vector and expression may be driven from its endogenous promoter or from the retroviral long terminal repeat or from a promoter specific for the target cell type of interest. Other viral vectors can be used and include, as is known in the art, adenoviruses, adeno-associated viruses, vaccinia viruses, papovaviruses, lentiviruses and retroviruses of avian, murine and human origin.

Gene therapy may be carried out according to established methods (See for example Friedman, 1991; Culver, 1996). A vector containing a nucleic acid molecule of the invention linked to expression control elements and capable of replicating inside the cells is prepared. Alternatively the vector may be replication deficient and may require helper cells for replication and use in gene therapy.

Gene transfer using non-viral methods of infection in vitro can also be used. These methods include direct injection of DNA, uptake of naked DNA in the presence of calcium phosphate, electroporation, protoplast fusion or liposome delivery. Gene transfer can also be achieved by delivery as a part of a human artificial chromosome or receptor-mediated gene transfer. This involves linking the DNA to a targeting molecule that will bind to specific cell-surface receptors to induce endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

In a still further aspect, there is provided a method of treating an angiogenesis-related disorder comprising administering a polypeptide, as described above, or an agonist thereof, to a subject.

In another aspect the invention provides the use of a polypeptide as described above, or an agonist thereof, in the manufacture of a medicament for the treatment of an angiogenesis-related disorder. Examples of such disorders are described above.

In a further aspect, a suitable agonist may also include peptides, phosphopeptides or small organic or inorganic compounds that can mimic the function of a polypeptide of the invention, or may include an antibody specific for a polypeptide of the invention that is able to restore function to a normal level.

Peptides, phosphopeptides or small organic or inorganic compounds suitable for therapeutic applications may be identified using nucleic acids and polypeptides of the invention in drug screening applications as described below.

In further embodiments, any of the agonists, antagonists, complementary sequences, siRNA molecules, shRNA molecules, nucleic acid molecules, polypeptides, antibodies, or vectors of the invention may be administered in combination with other appropriate pharmaceutical or therapeutic agents, or treatment methods. Selection of the appropriate agents and treatment methods may be made by those skilled in the art, according to conventional pharmaceutical principles. The combination of therapeutic agents and treatment methods may act synergistically to effect the treatment or prevention of the various disorders described above. Using this approach, therapeutic efficacy with lower dosages of each agent may be possible, thus reducing the potential for adverse side effects.

Any of the therapeutic methods described above may be applied to any subject, including, for example, mammals such as dogs, cats, cows, horses, rabbits, monkeys, and most preferably, humans.

Modulation of Angiogenesis

In a further aspect of the present invention, any of the methods described above used for the treatment of an angiogenesis-related disorder may be used for the modulation of angiogenesis in any system comprising cells. These systems may include but are not limited to, in vitro assay systems (e.g. Matrigel assays, proliferation assays, migration assays, collagen assays, bovine capillary endothelial cell assay etc), in vivo assay systems (e.g. in vivo Matrigel-type assays, chicken chorioallantoic membrane assay, isolated organs, tissues or cells etc), animal models (e.g. in vivo neovascularisation assays, tumour angiogenesis models etc) or hosts in need of treatment (e.g. hosts suffering from angiogenesis-related disorders as previously described).

Drug Screening

According to still another aspect of the invention, nucleic acid molecules of the invention as well as polypeptides, or fragments thereof of the invention, and cells expressing these, are useful for the screening of candidate pharmaceutical compounds in a variety of techniques for the treatment of angiogenesis-related disorders.

Still further, it provides the use wherein high throughput screening techniques are employed.

Molecules that interact with the nucleic acid molecules and polypeptides of the invention have been identified. Still further, a mutant of BNO69 in which the putative GAP activity of BNO69 is eliminated has been identified, specifically a mutant in which Arg82 of SEQ ID NO: 11 is replaced, more specifically in which Arg82 is replaced by Ala (hence an R82A mutation). Accordingly, in still another aspect of the invention, nucleic acid molecules encoding these as well as the polypeptides and cells and animals expressing these are useful for the screening of candidate pharmaceutical compounds in a variety of techniques for the treatment of angiogenesis-related disorders.

Compounds that can be screened in accordance with the invention include, but are not limited, to peptides (such as soluble peptides), phosphopeptides and small organic or inorganic molecules (such as natural product or synthetic chemical libraries and peptidomimetics).

In one embodiment, a screening assay may include a cell-based assay utilising eukaryotic or prokaryotic host cells that are stably transformed with recombinant nucleic acid molecules expressing the polypeptides, or fragments thereof, of the invention, in competitive binding assays. Binding assays will measure for the formation of complexes between the polypeptide, or fragments thereof, and the compound being tested, or will measure the degree to which a compound being tested will interfere with the formation of a complex between the polypeptide, or fragments thereof, and its interactor or ligand.

For example BNO69 is able to interact with multiple members of the Rho family in a cell-specific manner given that the effects of BNO69 knockdown on the activity of Rho, Rac and Cdc42 differs dependent upon the cell type. BNO69 knockdown increases Rho activity in endothelial cells but leads to no change in active Rac or Cdc42. This is in contrast to results in NIH3T3 cells where inhibition of BNO69 expression leads to an increase in Rac activity. This suggests that the GAP domain of BNO69 is able to bind to multiple members of the Rho family in a cell-specific manner. Accordingly the interactors of BNO69 may be a RhoGTPase as in endothelial cells or could be a RacGTPase as in NIH3T3 cells. Furthermore, disruption of the pathway that BNO69 is a part of (through introduction of an siRNA according to the invention or manipulation to introduce a mutant BNO69 in which GAP activity is reduced or eliminated in accordance with the invention) will alter the expression of other proteins in the pathway which allows identification of further drug targets in the pathway. Thus the interactor for polypeptides of the invention may be Rho, Rac, Cdc42 or other members of the Rho family, or other proteins in the pathway that BNO69 is a part of.

Non cell-based assays may also be used for identifying compounds that interrupt binding between the polypeptides of the invention and their interactors. Such assays are known in the art and include for example AlphaScreen technology (PerkinElmer Life Sciences, MA, USA). This application relies on the use of beads such that each interaction partner is bound to a separate bead via an antibody. Interaction of each partner will bring the beads into proximity, such that laser excitation initiates a number of chemical reactions ultimately leading to fluorophores emitting a light signal. Candidate compounds that disrupt the binding of the polypeptide with its interactor will result in loss of light emission enabling identification and isolation of the responsible compound.

High-throughput drug screening techniques may also employ methods as described in WO84/03564. Small peptide test compounds synthesised on a solid substrate can be assayed through polypeptide binding and washing. The bound polypeptide is then detected by methods well known in the art. In a variation of this technique, purified polypeptides can be coated directly onto plates to identify interacting test compounds.

An additional method for drug screening involves the use of host eukaryotic cell lines that carry mutations in a nucleic acid molecule of the invention. The host cell lines are also defective at the polypeptide level. Other cell lines may be used where the expression of the nucleic acid molecule of the invention can be regulated (i.e. over-expressed, under-expressed, or switched off). The host cell lines or cells are grown in the presence of various drug compounds and the rate of growth of the host cells is measured to determine if the compound is capable of regulating the growth of defective cells.

The polypeptides of the present invention may also be used for screening compounds developed as a result of combinatorial library technology. This provides a way to test a large number of different substances for their ability to modulate activity of a polypeptide. A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups that mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original binding site. The anti-id could then be used to isolate peptides from chemically or biologically produced peptide banks.

Another alternative method for drug screening relies on structure-based rational drug design. Determination of the three dimensional structure of the polypeptides of the invention, or the three dimensional structure of the protein complexes which may incorporate these polypeptides allows for structure-based drug design to identify biologically active lead compounds.

Three-dimensional structural models can be generated by a number of applications, some of which include experimental models such as x-ray crystallography and NMR and/or from in silico studies using information from structural databases such as the Protein Databank (PDB). In addition, three dimensional structural models can be determined using a number of known protein structure prediction techniques based on the primary sequences of the polypeptides (e.g. SYBYL—Tripos Associated, St. Louis, Mo.), de novo protein structure design programs (e.g. MODELER—MSI Inc., San Diego, Calif., or MOE—Chemical Computing Group, Montreal, Canada) or ab initio methods (e.g. see U.S. Pat. Nos. 5,331,573 and 5,579,250).

Once the three dimensional structure of a polypeptide or polypeptide complex has been determined, structure-based drug discovery techniques can be employed to design biologically active compounds based on these three dimensional structures. Such techniques are known in the art and include examples such as DOCK (University of California, San Francisco) or AUTODOCK (Scripps Research Institute, La Jolla, Calif.). A computational docking protocol will identify the active site or sites that are deemed important for protein activity based on a predicted protein model. Molecular databases, such as the Available Chemicals Directory (ACD) are then screened for molecules that complement the protein model.

Using methods such as these, potential clinical drug candidates can be identified and computationally ranked in order to reduce the time and expense associated with typical 'wet lab' drug screening methodologies.

Compounds identified from the screening methods described above form a part of the present invention, as do pharmaceutical compositions containing these and a pharmaceutically acceptable carrier.

Pharmaceutical Preparations

Compounds identified from screening assays as indicated above, as well as siRNA and shRNA molecules of the invention can be administered to a patient at a therapeutically effective dose to treat or ameliorate a disorder associated with angiogenesis. A therapeutically effective dose refers to that amount of the compound, siRNA, or shRNA molecules sufficient to result in amelioration of symptoms of the disorder.

Toxicity and therapeutic efficacy of such compounds or molecules can be determined by standard pharmaceutical procedures in cell cultures or experimental animals. The data obtained from these studies can then be used in the formulation of a range of dosages for use in humans.

Pharmaceutical compositions for use in accordance with the present invention can be formulated in a conventional manner using one or more physiological acceptable carriers, excipients or stabilisers which are well known. Acceptable carriers, excipients or stabilizers are non-toxic at the dosages and concentrations employed, and include buffers such as phosphate, citrate, and other organic acids; antioxidants including absorbic acid; low molecular weight (less than about 10 residues) polypeptides; proteins, such as serum albumin, gelatin, or immunoglobulins; binding agents including hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics or polyethylene glycol (PEG).

The formulation of pharmaceutical compositions for use in accordance with the present invention will be based on the proposed route of administration. Routes of administration may include, but are not limited to, inhalation, insufflation (either through the mouth or nose), oral, buccal, rectal or parental administration.

Diagnostic and Prognostic Applications

The nucleic acid molecules and polypeptides of the invention enable the diagnosis or prognosis of angiogenesis-related disorders, or a predisposition to such disorders. Examples of such disorders include, but are not limited to, cancer; inflammatory disorders including arthritis; corneal, retinal or choroidal neovascularization including macular degeneration and diabetic retinopathy; psoriasis; cardiovascular diseases. Diagnosis or prognosis may be used to determine the severity, type or stage of the disease state in order to initiate an appropriate therapeutic intervention.

In another embodiment of the invention, the nucleic acid molecules that may enable diagnosis or prognosis include polynucleotides such as oligonucleotides, genomic DNA and complementary RNA and DNA molecules corresponding to the nucleic acid molecules of the invention. The polynucleotides may be used to detect and quantitate gene expression in biopsied tissues in which abnormal expression of, or mutations in, a nucleic acid molecule of the invention may be correlated with disease. Genomic DNA used for the diagnosis or prognosis may be obtained from body cells, such as those present in the blood, tissue biopsy, surgical specimen, or autopsy material. The DNA may be isolated and used directly for detection or may be amplified by the polymerase chain reaction (PCR) prior to analysis. Similarly, RNA or cDNA may also be used, with or without PCR amplification. To detect a specific nucleic acid molecule, direct nucleotide sequencing, reverse transcriptase PCR (RT-PCR), hybridization using specific oligonucleotides, restriction enzyme digest and mapping, PCR mapping, RNAse protection, and various other methods may be employed. Oligonucleotides specific to a specific nucleic acid molecule can be chemically synthesized and labelled radioactively or nonradioactively and hybridized to individual samples immobilized on membranes or other solid-supports or in solution. The presence, absence or excess expression of a specific nucleic acid molecule may then be visualized using methods such as autoradiography, fluorometry, or colorimetry.

In a particular aspect, a polynucleotide corresponding to a nucleic acid molecule of the invention, as described above, may be useful in hybridisation assays that detect the presence of associated disorders, particularly those mentioned previously. The polynucleotide may be labelled by standard methods and added to a fluid or tissue sample from a patient under conditions suitable for the formation of hybridisation complexes. After a suitable incubation period, the sample is washed and the signal is quantitated and compared with a standard value. If the amount of signal in the patient sample is significantly altered in comparison to a control sample then the presence of altered levels of the nucleic acid molecule in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis or prognosis of an angiogenesis-related disorder associated with a mutation in a nucleic acid molecule of the invention, the nucleotide sequence of the nucleic acid molecule can be compared between normal tissue and diseased tissue in order to establish whether the patient expresses a mutant gene.

In order to provide a basis for the diagnosis or prognosis of a disorder associated with abnormal expression of a nucleic acid molecule of the invention, a normal or standard profile for expression is established. This may be accomplished by combining body fluids or cell extracts taken from normal subjects, either animal or human, with a nucleic acid molecule of the invention, under conditions suitable for hybridization or amplification. Standard hybridization may be quantified by comparing the values obtained from normal subjects with values from an experiment in which a known amount of a substantially purified polynucleotide is used. Another method to identify a normal or standard profile for expression of a nucleic acid molecule of the invention is through quantitative RT-PCR studies. RNA isolated from body cells of a normal individual, particularly RNA isolated from endothelial cells, is reverse transcribed and real-time PCR using oligonucleotides specific for the nucleic acid molecule is conducted to establish a normal level of expression of the gene. Standard values obtained in both these examples may be compared with values obtained from samples from patients who are symptomatic for a disorder. Deviation from standard values is used to establish the presence of a disorder.

Once the presence of a disorder is established and a treatment protocol is initiated, hybridization assays or quantitative RT-PCR studies may be repeated on a regular basis to determine if the level of expression in the patient begins to approximate that which is observed in the normal subject. The results obtained from successive assays may be used to show the efficacy of treatment over a period ranging from several days to months.

According to a further aspect of the invention there is provided the use of a polypeptide of the invention, as described above, in the diagnosis or prognosis of an angiogenesis-related disorder or a predisposition to such disorders.

When a diagnostic or prognostic assay is to be based upon a polypeptide of the invention, a variety of approaches are possible. For example, diagnosis or prognosis can be achieved by monitoring differences in the electrophoretic mobility of normal and mutant polypeptides. Such an approach will be particularly useful in identifying mutants in which charge substitutions are present, or in which insertions, deletions or substitutions have resulted in a significant change in the electrophoretic migration of the resultant polypeptide. Alternatively, diagnosis or prognosis may be based upon differences in the proteolytic cleavage patterns of normal and mutant polypeptides, differences in molar ratios of the various amino acid residues, or by functional assays demonstrating altered function of the polypeptides.

In another aspect, antibodies that specifically bind the polypeptides of the invention may be used for the diagnosis or prognosis of angiogenesis-related disorders, or in assays to monitor patients being treated with a polypeptide of the invention or agonists, antagonists, or inhibitors thereof. Antibodies useful for diagnostic or prognostic purposes may be prepared in the same manner as described above for therapeutics. Diagnostic or prognostic assays may include methods that utilize the antibody and a label to detect the relevant polypeptide in human body fluids or in extracts of cells or tissues. The antibodies may be used with or without modification, and may be labelled by covalent or non-covalent attachment of a reporter molecule.

A variety of assays for measuring the polypeptide based on the use of antibodies specific for the polypeptide are known in the art and provide a basis for diagnosing altered or abnormal levels of expression. Normal or standard values for expression are established by combining body fluids or cell extracts taken from normal mammalian subjects, preferably human, with antibody to the polypeptide under conditions suitable for complex formation. The amount of standard complex formation may be quantitated by various methods which are known in the art. Examples include, but are not limited to, enzyme-linked immunosorbent assays (ELISAs), radioimmunoassays (RIAs), immunofluorescence, flow cytometry, histology, electron microscopy, in situ assays, immunoprecipitation, Western blot etc. For example, using the ELISA technique an enzyme which is bound to the antibody will react with an appropriate substrate, preferably a chromogenic substrate, in such a manner as to produce a chemical moiety that can be detected for example by spectrophotomeric, fluorimetric or by visual means. Detection may also be accomplished by using other assays such as RIAs where the antibodies or antibody fragments are radioactively labelled. It is also possible to label the antibody with a fluorescent compound. When the fluorescently labelled antibody is exposed to light of a certain wavelength, its presence can then be detected due to fluorescence. The antibody can also be detectably labelled by coupling it to a chemiluminescent compound. The presence of the chemiluminescent-tagged antibody is then determined by detecting the presence of luminescence that arises during the course of a chemical reaction.

Quantities of polypeptide expressed in subject, control, and disease samples from biopsied tissues are compared with the standard values. Deviation between standard and subject values establishes the parameters for diagnosing or prognosing disease.

Once an individual has been diagnosed or prognosed with a disorder, effective treatments can be initiated, as described above. In the treatment of angiogenesis-related diseases which are characterised by uncontrolled or enhanced angiogenesis, the expanding vasculature needs to be inhibited. This would involve inhibiting the nucleic acid molecules or polypeptides of the invention.

In the treatment of angiogenesis-related diseases which are characterised by inhibited or decreased angiogenesis, approaches which enhance or promote vascular expansion are desirable. This may be achieved by enhancing, stimulating or re-activating the expression of the nucleic acid molecules or polypeptides of the invention.

Microarray

In further embodiments, complete cDNAs, oligonucleotides or longer fragments derived from any of the nucleic acid molecules described herein may be used as probes in a microarray. The microarray can be used to monitor the expression level of large numbers of genes simultaneously and to identify genetic variants, mutations, and polymorphisms. This information may be used to determine gene function, to understand the genetic basis of angiogenesis-related disorders, to diagnose or prognose angiogenesis-related disorders, and to develop and monitor the activities of therapeutic agents. Microarrays may be prepared, used, and analysed using methods known in the art. (For example, see Schena et al., 1996; Heller et al., 1997).

Transformed Hosts

The present invention also provides for the production of genetically modified (knock-out, knock-in and transgenic), non-human animal models comprising the nucleic acid molecules of the invention. These animals are useful for the study of the function of the nucleic acid molecule, to study the process of angiogenesis, to study the mechanisms of angiogenic disease as related to these molecules, for the screening of candidate pharmaceutical compounds for the treatment of angiogenesis-related disorders, for the creation of explanted mammalian cell cultures which express the encoded polypeptide or mutant polypeptide, and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to the relative ease in generating knock-in, knock-out or transgenics of these animals, their ease of maintenance and their shorter life spans. For certain studies, transgenic yeast or invertebrates may be suitable and preferred because they allow for rapid screening and provide for much easier handling. For longer term studies, non-human primates may be desired due to their similarity with humans.

To create an animal model based on the nucleic acid molecules of the invention, several methods can be employed. These include, but are not limited to, generation of a specific mutation in a homologous animal gene, insertion of a wild type human gene and/or a humanized animal gene by homologous recombination, insertion of a mutant (single or multiple) human gene as genomic or minigene cDNA constructs using wild type, mutant or artificial promoter elements, or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create transgenic mice in order to study gain of gene function in vivo, a nucleic acid molecule of the invention can be inserted into a mouse germ line using standard techniques such as oocyte microinjection. Gain of gene function can mean the overexpression of a nucleic acid molecule and its encoded polypeptide product, or the genetic complementation of a mutation of the nucleic acid molecule under investigation. For oocyte injection, one or more copies of the wild type or mutant nucleic acid molecule can be inserted into the pronucleus of a just-fertilized mouse oocyte. This oocyte is then reimplanted into a pseudo-pregnant foster mother. The liveborn mice can then be screened for integrants using analysis of tail DNA for the presence of the nucleic acid molecule. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

To generate knock-out mice or knock-in mice, gene targeting through homologous recombination in mouse embryonic stem (ES) cells may be applied. Knock-out mice are generated to study loss of gene function in vivo while knock-in mice allow the study of gain of function or to study the effect of specific mutations. Knock-in mice are similar to transgenic mice however the integration site and copy number are defined in the former.

For knock-out mouse generation, gene targeting vectors can be designed such that they disrupt (knock-out) the protein coding sequence of the relevant nucleic acid molecule in the mouse genome. Knock-out animals of the invention will comprise a functional disruption of a relevant nucleic acid molecule of the invention such that the gene does not express a biologically active product. It can be substantially deficient in at least one functional activity coded for by the nucleic acid molecule. Expression of the polypeptide encoded by the nucleic acid molecule can be substantially absent (i.e. essentially undetectable amounts are made) or may be deficient in activity such as where only a portion of the polypeptide product is produced. In contrast, knock-in mice can be produced whereby a gene targeting vector containing the relevant nucleic acid molecule can integrate into a defined genetic locus in the mouse genome. For both applications, homologous recombination is catalysed by specific DNA repair enzymes that recognise homologous DNA sequences and exchange them via double crossover.

Gene targeting vectors are usually introduced into ES cells using electroporation. ES cell integrants are then isolated via an antibiotic resistance gene present on the targeting vector and are subsequently genotyped to identify those ES cell clones in which the nucleic acid molecule under investigation has integrated into the locus of interest. The appropriate ES cells are then transmitted through the germline to produce a novel mouse strain.

In instances where gene ablation results in early embryonic lethality, conditional gene targeting may be employed. This allows genes to be deleted in a temporally and spatially controlled fashion. As above, appropriate ES cells are transmitted through the germline to produce a novel mouse strain, however the actual deletion of the relevant nucleic acid molecule is performed in the adult mouse in a tissue specific or time controlled manner. Conditional gene targeting is most commonly achieved by use of the cre/lox system. The enzyme cre is able to recognise the 34 base pair loxP sequence such that loxP flanked (or floxed) DNA is recognised and excised by cre. Tissue specific cre expression in transgenic mice enables the generation of tissue specific knock-out mice by mating gene targeted floxed mice with cre transgenic mice. Knock-out can be conducted in every tissue (Schwenk et al., 1995) using the 'deleter' mouse or using transgenic mice with an inducible cre gene (such as those with tetracycline inducible cre genes), or knock-out can be tissue specific for example through the use of the CD19-cre mouse (Rickert et al., 1997).

According to still another aspect of the invention there is provided the use of genetically modified non-human animals for the screening of candidate pharmaceutical compounds.

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

BRIEF DESCRIPTION OF THE DRAWINGS

FIG. 3: Effect of BNO69 knock-down in HUVECs on the activity of Rho, Rac and Cdc42. BNO69 has activity for Rho but not Rac and Cdc42 in HUVECs. HUVECs were adenoviral infected with empty vector (EV), BNO69R and BNO69 mutant (R82A) and incubated without serum for 20 h. The cells were lysed and assayed for detection of active Rho-GTP, Rac-GTP and Cdc42-GTP, and the average fold increase compared to empty vector (EV) is shown. Each result represents at least 4 independent experiments.

FIG. 5: BNO69 regulates stress fibre formation. HUVECs were adenoviral infected with empty vector (EV) (A) or BNO69R (B & C) or were retrovirally infected with empty vector (D) or BNO69.3 siRNA (SEQ ID NO: 3) (E), 24 h prior to plating on fibronectin. BNO69R infected HUVECs were treated without (B) or with (C) C3 exoenzyme (30 µg/ml) for 32 h and stained with rhodamine-phalloidin. Retrovirally infected HUVECs (empty vector and BNO69.3 siRNA) were stained with FITC-phalloidin and the nuclei were stained with DAPI.

FIG. 10: BNO69 expression silencing inhibits HUVEC migration. HUVECs infected with BNO69.3 (SEQ ID NO: 3) siRNA or a vector control, were allowed to migrate towards fibronectin for 24 hrs. Cells infected with BNO69.3 siRNA exhibited substantially reduced migration ability as compared to cells infected with the vector control.

FIG. 12: Real-time RT-PCR expression analysis of BNO69 isoforms I and III in a range of tumour cell line samples.

FIG. 14: Analysis of the effect of BNO69.4 (SEQ ID NO: 4) siRNA on proliferation in a range of tumour cell lines.

FIG. 15: Analysis of the effect of BNO69.3 (SEQ ID NO: 3) siRNA and BNO69.4 (SEQ ID NO: 4) siRNA on migration in a range of tumour cell lines.

Figure 1:
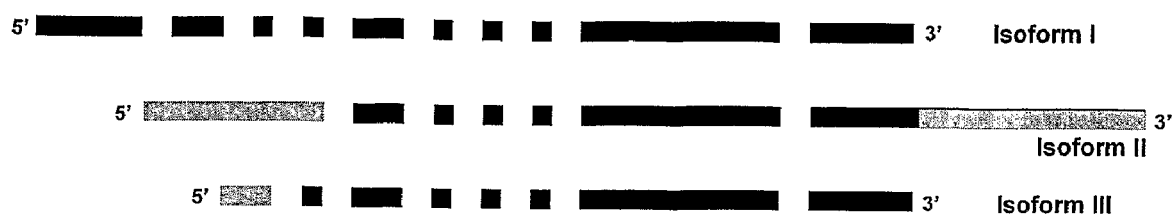
FIG. 1: BNO69 splicing isoforms identified by in silico analysis of representative EST sequences in dbest.

The invention will now be described in detail by way of reference to the following non-limiting example.

EXAMPLE

Identification and Functional Analysis of BNO69 Isoforms

Materials and Methods

Endothelial Cell Culture and Infection

Human umbilical vein endothelial cells (HUVECs) were purchased from Clonetics (cc-2519) and cultured in EGM-2 Bullet kit (Clonetics α-3162). Cells were subcultured weekly up to a maximum of 6 passages.

Tumour Cells and Cell Culture

The MDA-MB-231 breast adenocarcinoma cell line was obtained from ATCC (Cat. HBT-26), and cultured in RPMI medium (Gibco, Cat. 21870-076) supplemented with 10% foetal bovine serum (FBS; JRH Biosciences), 10 mM HEPES (Gibco, Cat. 15630-080), 1 mM sodium pyruvate (Gibco, Cat. 11360-070), and 1% penicillin/streptomycin/glutamine (PSG; Gibco, Cat. 10378-016). Media was replaced with fresh media every 2-3 days and cells were subcultured once a week at a subcultivation ratio of 1:4 for up to three months. The U-87MG brain glioblastoma cell line was obtained from ATCC (Cat. HTB-14), and cultured in EMEM medium (Eagles minimum essential medium, MultiCel, Cat. 11-050-0500V) supplemented with 10% foetal bovine serum (FBS; JRH Biosciences), 10 mM HEPES (Gibco, Cat. 15630-080), 1 mM sodium pyruvate (Gibco, Cat. 11360-070), 0.1 mM non-essential amino acids (NEAA; Gibco, Cat. 11140-05) and 1% penicillin/streptomycin/glutamine (PSG; Gibco, Cat. 10378-016). Media was replaced with fresh media every 2-3 days and cells were subcultured once a week at a subcultivation ratio of 1:5 for up to three months. All tumour cells used (see FIG. 12 for complete cell line details) were maintained in a humidified incubator at 37° C. in 5% $CO_2$ in air.

Generation of Recombinant BNO69 Clones

HUVEC RNA was isolated and cDNA generated by reverse transcription. Primers were designed to amplify BNO69 5' and 3' cDNA fragments. Both PCR products were cloned into the pGEM-Teasy vector (Promega), confirmed by sequencing and ligated together via a common internal BamHI site. To generate the BNO69 mutant (R82A), the arginine codon (CGA) at position 82 of BNO69 isoform II was changed to alanine (GCA) using a PCR mutagenesis approach. The BNO69 or R82A mutant cDNA were excised from pGEM-Teasy with NotI and subcloned (in both orientations for BNO69) into the shuttle vector pAdTrack-CMV (Qbiogene). 5'-FLAG-tagged-BNO69 was generated by PCR and cloned into the EcoRV site of pAdTrack-CMV. Recombinant adenovirus was made using the pAdEasy system (Qbiogene). Viral titres were determined using the $TCID_{50}$ method and viral particle number quantified at OD 600 nm.

For gene transfer experiments, cells were grown to 80% confluence and infected with an amount of pAdEasy empty vector (EV), pAdEasy-BNO69 antisense (BNO69R), pAdEasy-BNO69 sense (BNO69F) or pAdEasy-BNO69R82A (R82A) mutant virus particles which yielded a similar level of GFP expression.

Generation of a Retroviral Vector Expressing the BNO69.3 siRNA and BNO69.4 siRNA Sequences The pMSCVpuro (BD Biosciences) was modified to create a short hairpin RNA (shRNA)-generating retroviral vector. To do this, the 3'LTR of pMSCVpuro was inactivated by removal of a XbaI/NheI fragment. A HL-RNA Polymerase III promoter cassette was then inserted into the multiple cloning site (MCS) of the vector. The BNO69.3 siRNA sequence (SEQ ID NO: 3) or the BNO69.4 siRNA sequence (SEQ ID NO: 4) was cloned into the modified pMSCVpuro vector in a short hairpin sequence format. The shRNA format comprises the siRNA sequence followed by a generic 9 nucleotide sequence, followed by the reverse complement of the siRNA. The shRNA sequences corresponding to BNO69.3 and BNO69.4 are represented by SEQ ID Numbers: 6 and 7 respectively. Upon integration in the host cell genome the siRNA forms a double stranded structure by annealing to its reverse complement. The 9 nucleotide generic sequence forms a loop at one end of the double stranded molecule. Negative controls included the sequence 5'-AGGCAT-CAGCGGACCTCAT-3' (SEQ ID NO: 18) as this contained similar GC content as to BNO69.3 siRNA and BNO69.4 siRNA, or a vector-only construct.

Retroviral Particle Production 293T cells (ATCC Cat. CRL-11268) were plated at a density of $1.7 \times 10^7$ cells per T175 flask 18-24 hours pre-transfection in RPMI media supplemented with 10% FCS without antibiotics. Cells were co-transfected with 28 μg retroviral vector (DNA), 23 μg pVPack VSV-G, 23 μg pVPack GP using LF2000 (Invitrogen) reagent. Transfected cells were incubated overnight at 37° C. in 5% $CO_2$. The following day media containing the DNA/LF2000 complexes was removed and replaced with RPMI supplemented with 10% FCS, 1M HEPES and 1% PSG. Virus containing supernatants were collected 48-72 hours post-transfection, centrifuged to pellet cell debris and then filtered using a sterile 0.45 μm filter. Virus was aliquoted and stored at −80° C. Viral titre was determined utilizing viral supernatants in serial dilution to infect NIH-3T3 cells, which were then cultured under puromycin selection for 7 days.

Retroviral Infection of HUVE Cells

HUVE cells were plated in EGM-2 complete media at a density of $1.3 \times 10^5$ cells per well of a 6 well plate. 500 μl of virus supernatant was combined with 500 μl of EGM-2 complete media. Polybrene was added to a final concentration of 8 μg/ml. Cells were incubated with the viral mix at 37° C. 5% $CO_2$. Following 3 hours incubation an additional 11.0 ml of EGM-2 media was added and cells were incubated for a further 24 hours. Subsequently, cells were incubated in EGM-2 complete medium containing puromycin (0.35 μg/ml final concentration). Cells were incubated until uninfected cells treated with puromycin had died and infected resistant cells had grown to confluence. Media containing puromycin was replaced every 48 hours to replenish puromycin and remove cell debris. Once resistant cells were grown to confluence (approximately 4-5 days after starting selection), cells were washed in PBS and trypsinised prior to their use.

Retroviral Infection of Tumour Cells

Tumour cells (for each cell line) were plated out at a density of $2 \times 10^6$ cells per T175 flask 18-24 hours pre-infection in supplemented RPMI media as described earlier. At infection, media was aspirated from the flasks and viral supernatant was added to an m.o.i. of 1:10 in a total of 15 mls supplemented RPMI media containing polybrene at a final concentration of 8 μg/ml. Cells were incubated with the viral mix at 37° C. for 4 hours in humidified conditions in 5% $CO_2$ in air. Following this incubation an additional 25 mls of media was added to each flask and the cells were incubated for a further 24 hours. Fresh media was subsequently added to the cells for the next 24 hours and then cells were grown under puromycin selection (0.6 μg/ml) until uninfected cells treated with puromycin had died and infected resistant cells had grown to confluence. Media containing puromycin was replaced every 48 hours in order to replenish puromycin and also remove cell debris. Once resistant cells were selected (4-5 days after starting selection), cells were washed in PBS, trypsinized and either resuspended in Dulbecco's PBS with Calcium and Magnesium (SIGMA, Cat. D8662) for injection into animals or plated out for the proliferation assay or the migration assay as outlined below. Cells were infected with viral particles depending on the experiment conducted: pMSCVpuro-vector alone (no DNA insert), pMSCVpuro-BNO69.3 siRNA or pMSCVpuro-BNO69.4 siRNA. Additionally untreated cells were cultured and harvested on the same day as the infected cells contributing as another control group to each experiment.

Expression Analysis in HUVE Cells

Real-time RT-PCR was utilized to perform expression analysis. Total RNA was isolated from HUVE cells using the RNeasy Mini kit (Qiagen) as per manufacturer's instructions including the on-column DNase treatment. Total RNA was visualised on a 1.2% TBE agarose gel containing ethidium bromide to check for quality and purity. Total RNA concentration was determined by $A^{260}$ on a spectrophotometer. Total RNA (1 ug/ul) was reverse transcribed using M-MLV (Promega) as per manufacturer's directions. Real-Time PCR was run on the RotorGene™ 2000 (Corbett Research). Reactions used AmpliTaq Gold enzyme (Applied Biosystems) and followed manufacturer's instructions. Cycling conditions were typically 94° C. for 12 minutes, 35 cycles of 94° C. for 15 s, 57° C. for 15 s, 72° C. for 20 s. All data were normalised to the expression of the housekeeping gene POLR2K (RNA polymerase II).

Expression Analysis in Tumour Cells

Real-time RT-PCR was utilized to perform expression analysis. Total RNA was isolated from all cell lines using the RNeasy Mini Kit (Qiagen Cat. 74103) as per manufacturer's instructions including the on-column DNase treatment. Total RNA was visualised on a 1.2% TBE agarose gel containing ethidium bromide to check for quality and purity of the RNA. Total RNA concentration was determined by A260 on a spectrophotometer. Total RNA (1 μg/μl) was reverse transcribed using M-MLV (Promega) as per manufacturer's instructions. Real-time PCR was run on the RotorGene™ 2000 (Corbett research). Reactions used AmpliTaq Gold enzyme (Applied Biosystems) and followed the manufacturer's directions. Cycling conditions were typically 94° C. for 12 minutes, 35 cycles of 94° C. for 15 secs, 57° C. for 15 seas, 72° C. for 20 seas with some optimization required for selected primer pairs. All data were normalised to the expression of the housekeeping gene POLR2K (RNA polymerase II).

Proliferation Assay—HUVE Cells

Infected cells were plated at 1000 cells/well in EBM+0.5% FBS in a 96 well plate in triplicate. Cells were cultured overnight at 37° C. 5% $CO_2$. Proliferation was induced by addition of the angiogenic growth factors VEGF (10 ng/ml) and bFGF (10 ng/ml) or EBM+0.5% FBS alone as a negative control. Medium was replaced every 48 hours and MTT assays were performed at time points. Briefly, 20 µl of MTT reagent was added to cells containing 100 µl of EBM+0.5% FBS and incubated at 37° C. for 2 hours. Absorbance was measured at 492 nm.

Proliferation Assay—Tumour Cells

For short term assays (time points up-to 96 hours post seeding) infected cells were plated at 1000 cells/well in 200 µl supplemented RPMI media (as described above), in a 96 well plate in triplicate. MTT assays were performed at 24 hour time points up-to 96 hours post seeding of cells. For long term assays (associated with xenograft experiments) infected cells were plated at 200 cells/well in 200 µl supplemented RPMI media (as described above), in a 96 well plate in triplicate. Medium was replaced every 7 days and MTT assays were performed at each measurement time point as specified below for each xenograft experiment. To conduct the proliferation assay the following steps were performed: initially media was aspirated from the wells and 100 µl of fresh media was added followed by 20 µl of MTT reagent (Promega Cat. G3581). Cells were incubated for 2 hours at 37° C. Absorbance was measured at 492 nm.

Matrigel Assay—HUVE Cells

Infected HUVECs were plated in 96 well plates at $2.5 \times 10^4$ cells/well. Wells were pre-coated with 50 ul Matrigel (Becton Dickinson) in EGM-2 media. HUVECs were allowed to form tubes by incubation at 37° C. at 5% $CO_2$ for 22 hrs.

Migration Assay—HUVE Cells

The migration assays were carried out in Neuroprobe ChemoTX 96 well plates with 8 um pore size filter. The underside of the filter was coated with 40 ul of 5 ug/ml fibronectin (or NIH3T3 conditioned medium for the MDA-MB231 assay) and incubated at RT for 1 hour. HUVECs were harvested and washed in MCDB 131 media +0.1% BSA. $5 \times 10^4$ cells were seeded per well in 40 ul media and incubated at 37° C. for 24 hours. Cells on the underside of the filter were fix/stained with 1% Crystal Violet/20% methanol. Stain was quantified by addition of 10 ul 33% acetic acid and absorbance read at 540 nm.

Migration Assay—Tumour Cells

The migration assay was carried out in Neuroprobe ChemoTX 96 well plates with 8 um pore size filter. Cells were harvested and washed in media +0.1% BSA. $5 \times 10^4$ cells were seeded per well in 40 ul media and incubated at 37° C. for 12 hours. Lower chambers were filled with NIH 3T3 conditioned media. Following the 12 hr incubation period cells on the underside of the chemotactic filter were fix/stained with 1% Crystal Violet/20% methanol. Stain was quantified by addition of 100 ul 33% acetic acid and absorbance read at 540 nm. Picture files of the underside of each chemotactic membrane were captured using a 4× objective on an Olympus BX51 microscope with a CCD Optronics high resolution camera. All samples were tested in triplicate.

F-actin Staining

Endothelial cells were plated on fibronectin coated LAB-TEK® Chamber Slides (Nalge, Nunc Int.). The cells were grown with or without C3 exoenzyme (30 µg/ml) for 32 h and then serum starved overnight also in the presence and absence of C3 exoenzyme. Cells infected with adenovirus containing antisense BNO69 were stained with rhodamine-phalloidin (Molecular Probes Inc.) while cells infected with retrovirus containing BNO69.3 siRNA were stained with FITC-phalloidin (Sigma) and nuclei were stained with DAPI (Vector Laboratories Inc.) The actin filaments were observed using an epi-fluorescence microscope.

Rho-, Rac- and Cdc42-GTP Activity Assays

Cells were serum depleted (EBM, Clonetics) overnight. Rho, Rac and Cdc42 activity was measured using the EZ-Detect™ Rho, Rac or Cdc42 Activation Kit (Pierce Biotechnology). Active protein was detected by western blotting using the monoclonal antibodies against Rho, Rac or Cdc42.

Rac-GTP Activity Assay

NIH3T3 cell lines transduced with retrovirus containing antisense BNO69 (BNO69R) or empty vector (EV) were serum starved overnight and lysed. Active RacGTP was pulled down by binding to the p21 binding domain (from p21 activated kinase) GST fusion protein and glutathione-sepharose. The sepharose-bound fraction and total cell lysate were Western blotted and probed with anti-Rac antibody.

Soft Agar Assay

Cells ($5 \times 10^5$) were placed in a DMEM medium/0.3% agarose suspension and cultured over 2 weeks in the presence of either BNO69.3 siRNA or vector only control on plates pre-coated with DMEM/0.7% agarose at 37° C./5% $CO_2$.

Athymic Nude Mice

Female athymic BALB/c-nu/nu mice were used for this study. Mice were between 6-8 weeks old and were purchased from ARC Western Australia and allowed to acclimatize for a couple of days. All the animals were housed under pathogen-free conditions and cared for in accordance with Flinders University of SA and NH&MRC guidelines and the Australian Code of Practise for the care and use of animals for scientific purposes.

Orthotopic Tumour Model

MDA-MB-231 cells untreated or infected and puromycin selected as described earlier were injected into each female athymic mouse. Each mouse was injected with $2 \times 10^6$ cells in 50 µl Dulbecco's PBS subcutaneously just above the mammary fat pad, below the right forward limb. Each group of mice were housed in a separate cage and tumour growth was measured using digital calipers and animals checked for health, three times a week for approximately 5 weeks. Tumour volume were calculated as a product of length× width×height. At the end of the experiment, the mice were sacrificed, the tumours resected, photographed and then frozen in OCT Compound (Tissue-Tek; Sakura) in liquid nitrogen and stored at −80° C. until sectioned.

Histology

Frozen tumours from all mice were cut utilizing a cryostat; sections of 10 µm thick were cut. Sections were subsequently fixed, stained with biotin conjugated rat α-mouse CD31 primary antibody (1:200 dilution, Pharmingen) for 4 hours followed by a 20 minute incubation with Extra Avidin (1:80 dilution, SIGMA Cat. E-4889). Further staining was performed with a 10 minute incubation with Fast Red (SIGMA FAS™ Fast Red TR/Napthol AS-MX, Cat. F-4648), followed by a final step of a 5 minute incubation with Mayer's Haematoxylin (SIGMA Cat. MHS-1). Slides were mounted and sections viewed under an Olympus BX51 microscope. Sections were photographed (5 fields per section) and area representing capillaries captured and analysed by image analysis software (ImageJ).

Statistical Analysis—Tumour Cells and Xenograft Models

Proliferation and migration data are presented as mean ±SD, and analysis done utilising unpaired two-tailed t-tests to determine differences between each treatment group (pMSCV-BNO69.3 siRNA or pMSCV-BNO69.4 siRNA) and the control group (pMSCVpuro-vector alone). Xenograft data are presented as mean ±SEM. Analysis of variance (ANOVA) was performed to determine differences between groups at each time point with Tukey's as the post-hoc test. All statistical analyses utilized GraphPad PRISM software (Version 4; GraphPad Software Inc.) A value of $p<0.05$ was considered statistically significant.

Results/Discussion

Identification of BNO69 Isoforms and Analysis of their GAP Activity

Identification of regulated genes during angiogenesis may result in characterisation of novel targets for therapeutic drug development. To this end, we have utilised a model of in vitro angiogenesis, where the morphological events and the time course of changes have been well characterised (Gamble et al., 1999; Meyer et al., 1997). Human umbilical vein endothelial cells, plated onto a 3-D collagen gel in the presence of growth factors, PMA and an antibody to the integrin, $\alpha 2\beta 1$, are induced to make capillary tubes over a 24 hour period. Isolation of these cells at critical time points, namely 0, 0.5, 3, 6 and 24 hours, and utilising a PCR based suppression subtractive hybridisation approach allowed the isolation of regulated genes.

Figure 2:
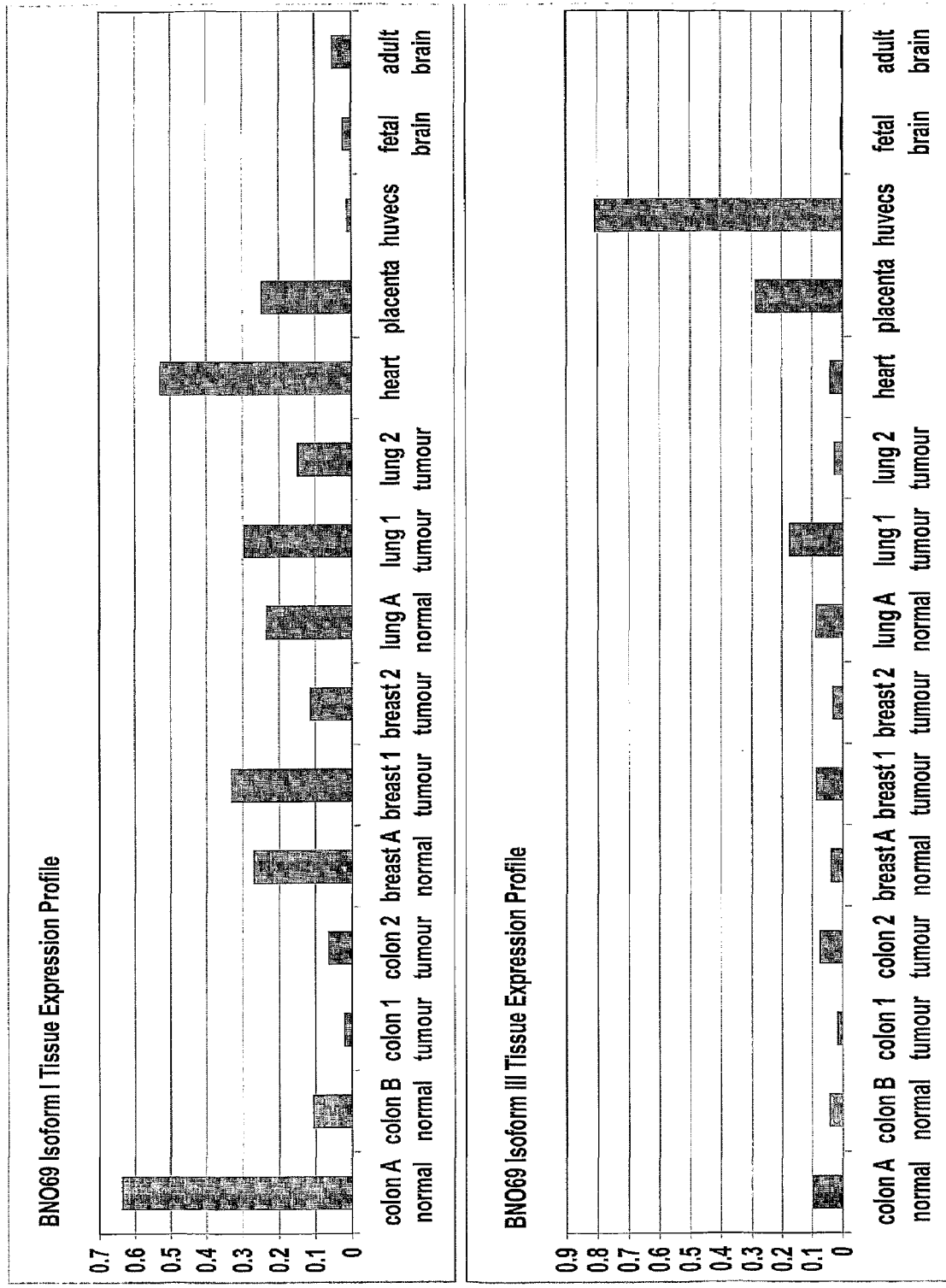
FIG. 2: Real-time RT-PCR expression analysis of BNO69 isoforms I and III in a range of human normal and tumour tissue samples. BNO69 isoform III exhibits preferential expression in HUVECs.

One of these genes was BNO69 which encodes a novel protein that contains a GTPase Activating Protein (GAP) domain suggesting that the gene may have GAP activity. In silico analysis of EST sequences corresponding to BNO69 retrieved from the dbest database using BLAST (National Centre for Biotechnolociy Information) enabled the assembly of three major BNO69 mRNA transcripts that appear to constitute the products of alternative exon splicing events (FIG. 1). We performed real time RT-PCR analyses to confirm the existence of these isoforms. Our data indicate that the predominantly expressed isoforms are I and III. Isoform I was found to be expressed at low levels in HUVECs, however in contrast, isoform III exhibited preferential expression in HUVECs (FIG. 2). All three isoforms contained the GAP domain.

A comparison of the GAP domain of BNO69 with those of other GAP proteins revealed considerable homology to other known RhoGAP containing proteins such as Bcr, N-chimerin, p50RhoGAP and p190RhoGAP. This region of homology comprises ~160 amino acid residues with 10 residues critical to the structural integrity of the GAP domain, 3 residues (Arg85, Asn188 and Lys172 with respect to the p50RhoGAP domain) catalytically crucial to GAP activity, and 5 residues (Gly82, Leu132, Leu178, Met190 and Asn194) that promote GTP hydrolysis (Rittinger et al., 1997; Barrett et al., 1997; Musacchio et al., 1996). The BNO69 protein has 9 of the 10 residues involved in the structural integrity of the GAP domain, with one conservative change from Leu to Ile. All three catalytic amino acids and four of the five GTP hydrolysis-promoting residues are identical with one conservative change of Leu to Val. The highly conserved identity suggests that BNO69 may have GAP activity.

Figure 4:
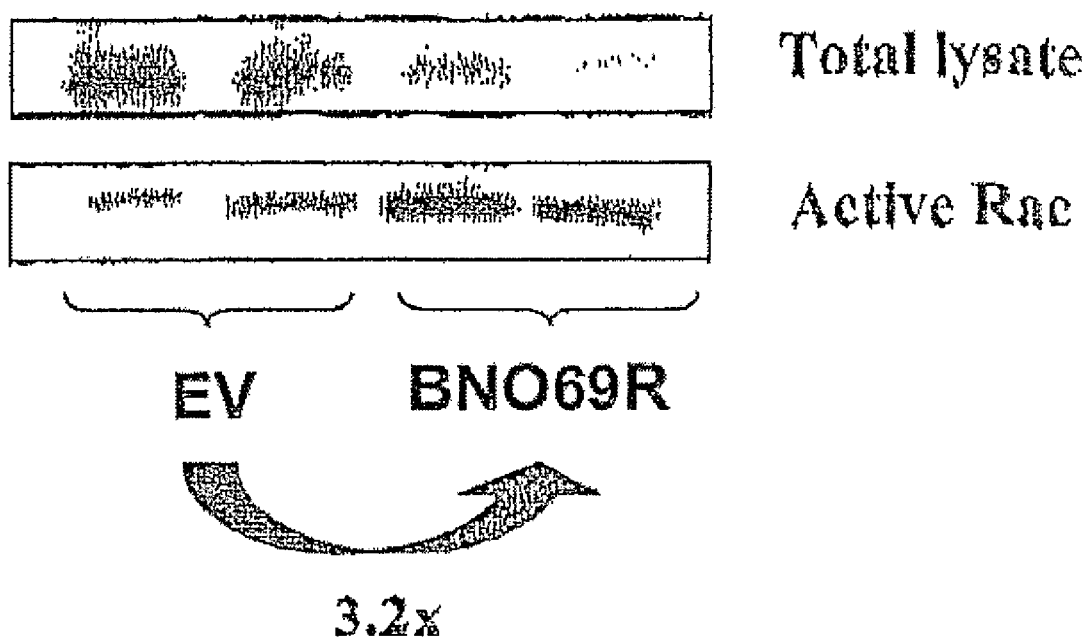
FIG. 4: Effect of BNO69 knock-down in NIH3T3 cells on the activity Rac. BNO69 has activity for Rac in NIH3T3 cells.

In order to test this hypothesis, adenovirus expressing antisense constructs of BNO69 (BNO69R) were delivered to endothelial cells in order to examine the effects of BNO69 knockdown on the activity of Rho, Rac and Cdc42. The results in FIG. 3 show that BNO69R increased Rho activity in endothelial cells compared to empty vector (EV) infected control cells. In 5 experiments performed, there was a 3.1±0.5 fold increase in Rho activity with BNO69R. No change in active Rac or Cdc42 (fold increase of 1.1±0.3 in both cases) with BNO69R was seen confirming that the BNO69 protein contains an active RhoGAP domain that has specificity in endothelial cells for Rho and not Rac or Cdc42. This is in contrast to results observed in NIH3T3 cells (FIG. 4) where inhibition of BNO69 expression using retroviral vectors expressing antisense BNO69 (BNO69R) lead to an approximately 3-fold increase in Rac activity. This suggests that the GAP domain of BNO69 is able to bind to multiple members of the Rho family in a cell-specific manner.

From protein structural analysis, the highly conserved Arg residue corresponding to Arg85 in p50RhoGAP is critical for the binding to Rho target proteins and increasing hydrolysis of Rho-bound GTP (Rittinger et al., 1997; Barrett et al., 1997; Musacchio et al., 1996). This amino acid residue corresponds to Arg82 in BNO69 (based on the numbering of BNO69 isoform II) which we mutated to Ala (R82A). Expression of this mutant in endothelial cells showed a 2.6±0.7 fold increase (n=4 experiments) in Rho activity (FIG. 3), consistent with this mutation both eliminating the GAP activity of BNO69 and generating a dominant negative form, further confirming that BNO69 indeed is a RhoGAP family member.

Consistent with Rho activity in endothelial cells, BNO69R and BNO69.3 siRNA infected endothelial cells showed increased stress fibre formation compared to empty vector control cells which displayed the classic cortical actin type morphology with minimal stress fibres, characteristic of unstimulated endothelial cells (FIG. 5A and FIG. 5D). In contrast, BNO69R and BNO69.3 siRNA infected endothelial cells displayed prominent, thick F-actin bundles (stress fibres), aligned in parallel arrays (FIG. 5B and FIG. 5E respectively). To confirm the effects of stress fibre formation were mediated by Rho, BNO69R infected HUVECs were treated with the Rho specific inhibitor, C3 transferase and then stained for F-actin. In the presence of C3 transferase, stress fibre formation was abolished (FIG. 5C), suggesting that the stress fibres are induced in the BNO69R infected cells, through an alteration in Rho.

BNO69.3 siRNA Inhibits HUVE Cell Function

Figure 6:
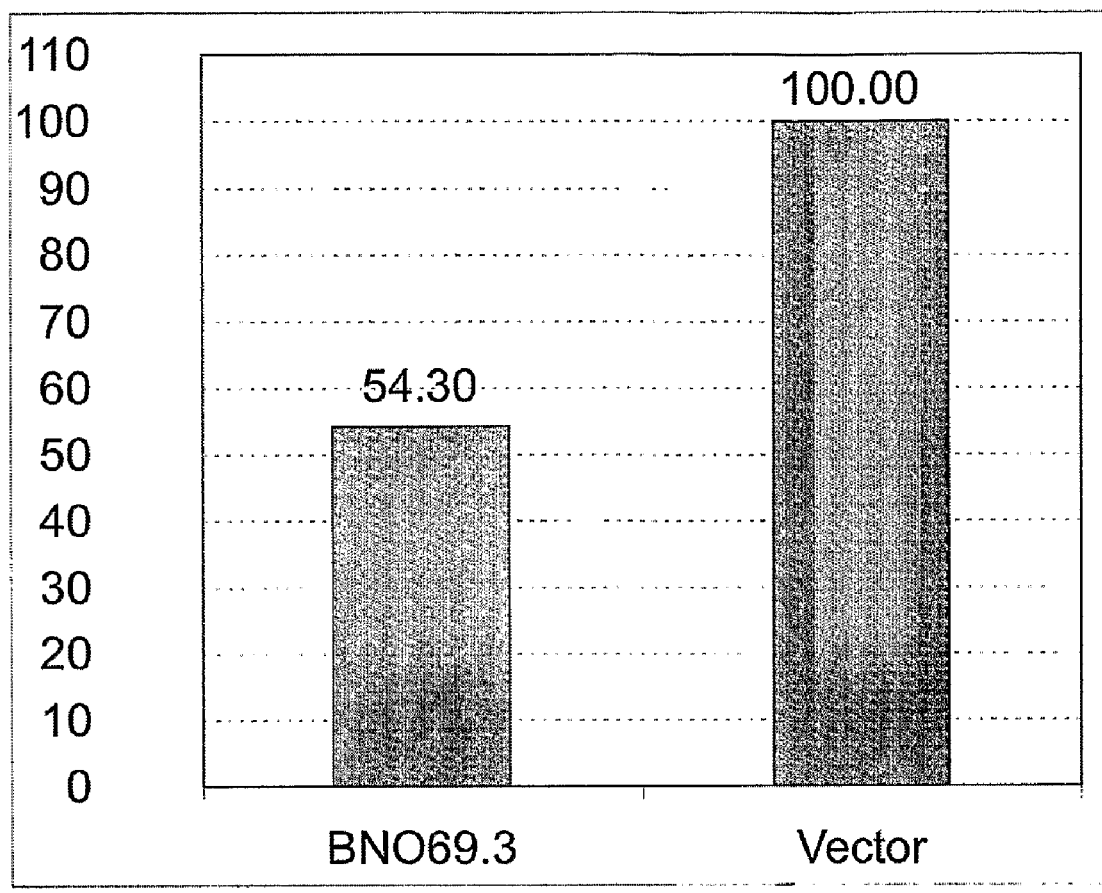
FIG. 6: Real-Time RT-PCR analysis of BNO69 expression knock-down in HUVECs mediated by BNO69.3 (SEQ ID NO: 3) siRNA. BNO69 mRNA expression in shRNA infected cells is expressed as a percentage of this gene's expression in HUVEC infected with the vector control. BNO69.3 siRNA silenced total BNO69 mRNA expression by approximately 50%.

To determine the role of BNO69 in angiogenic processes and on endothelial cell function, studies of the effect of siRNA-mediated silencing of BNO69 gene expression were conducted. Initially, HUVECs were infected with retroviral vectors expressing a range of short hairpin RNA (shRNA) sequences specific for BNO69. BNO69 mRNA levels were then determined by quantitative real-time RT-PCR and compared to BNO69 levels in cells infected with a vector-only control. Expression of RNA polymerase was used for data normalisation. These studies assessed the efficiency of the shRNA probes in silencing expression of the BNO69 mRNA. BNO69.3 siRNA silenced expression of BNO69 by approximately 50% (FIG. 6) and was used for subsequent experiments. These studies incorporated systems for examination of changes to endothelial cell function such as determination of cell proliferation changes, cell migration changes and effects on capillary tube formation, which are all essential features of the angiogenic process.

Figure 7:
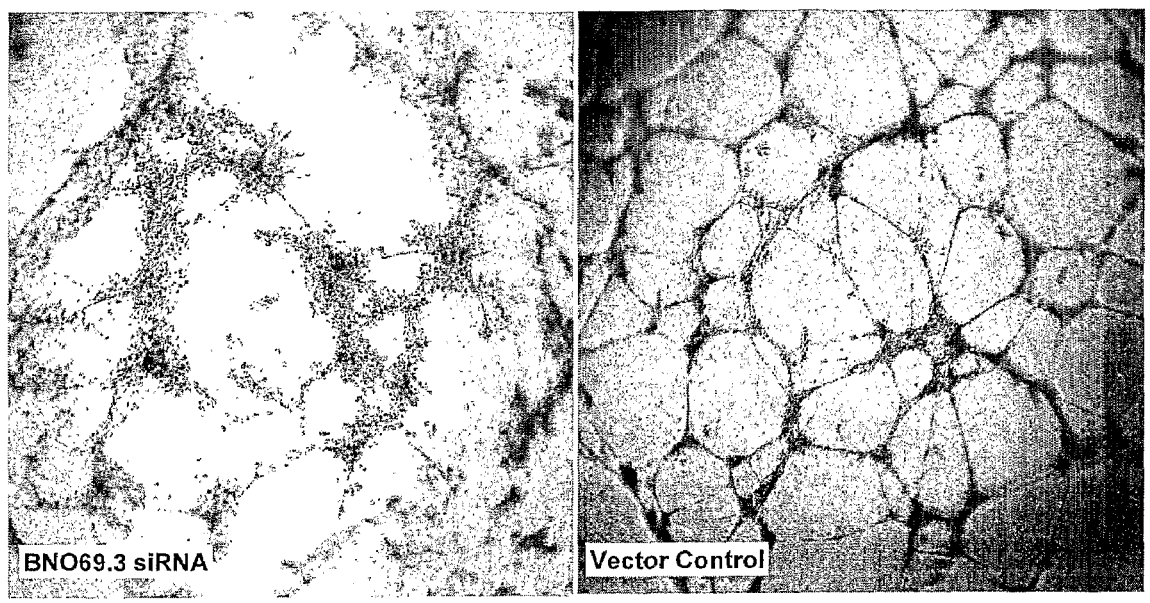
FIG. 7: Silencing BNO69 mRNA expression inhibits HUVEC tube formation. HUVECs infected with BNO69.3 (SEQ ID NO: 3) siRNA or a vector control were plated on Matrigel for 24 hrs. Vector control infected cells formed tube structures whereas cells infected with BNO69.3 siRNA failed to form tubes.
Figure 8:
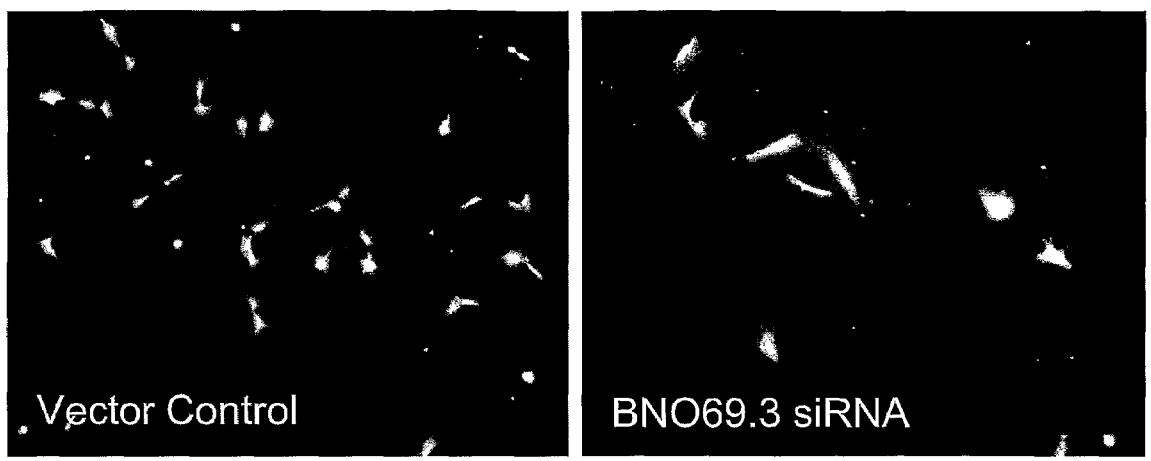
FIG. 8: BNO69 expression silencing results in HUVEC enlargement in culture. Images of cells infected with BNO69.3 (SEQ ID NO: 3) siRNA and a vector control are shown.
Figure 9:
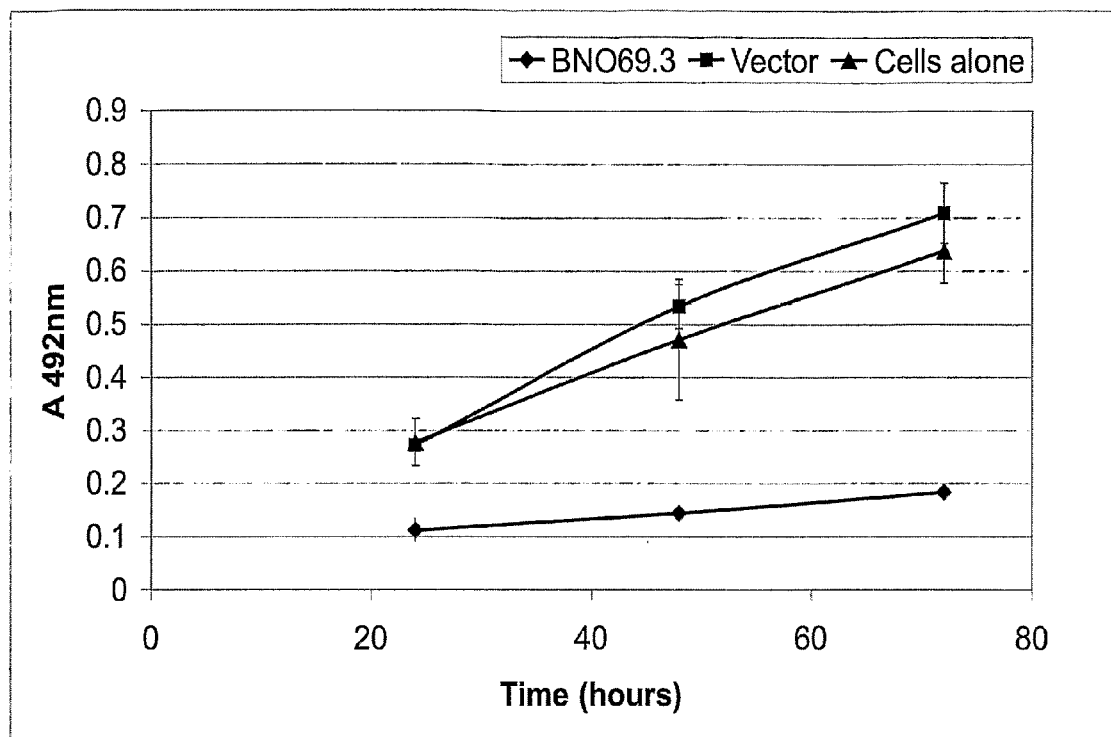
FIG. 9: BNO69 expression silencing inhibits HUVEC proliferation. HUVECs infected with BNO69.3 (SEQ ID NO: 3) siRNA or a vector control, were cultured for 72 hrs in complete medium and cell numbers were measured using an MTT assay. Cells infected with BNO69.3 siRNA exhibited substantially reduced growth compared to cells infected with the vector control.
Figure 11:
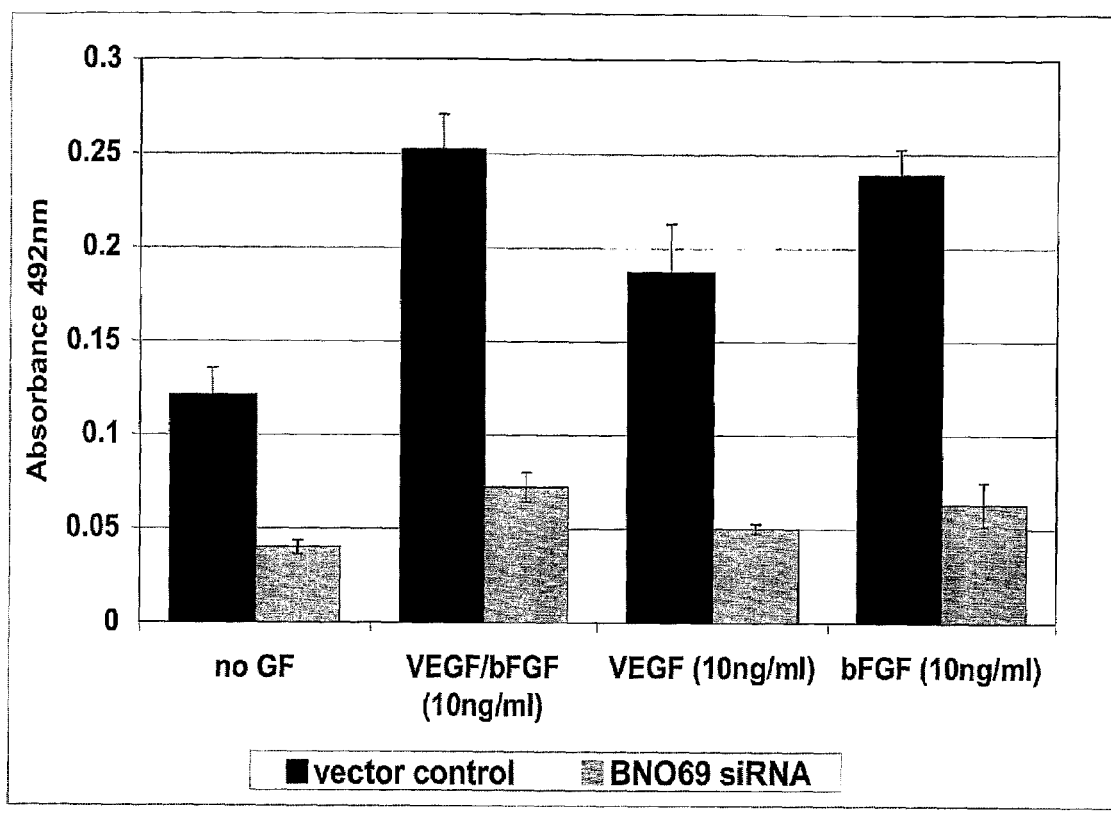
FIG. 11: Proliferation induction signalling. HUVECs infected with BNO69.3 (SEQ ID NO: 3) siRNA or a vector control were cultured in basic medium in the presence or absence of the pro-angiogenic growth factors VEGF and bFGF. These growth factors induced proliferation increase in vector-infected cells but failed to activate proliferation in cells infected with a BNO69.3 siRNA.

These experiments established that HUVECs infected with the BNO69.3 siRNA were unable to form capillary tubes when cultured on Matrigel. As can be seen in FIG. 7, vector-only infected cells formed tube structures (right panel) while cells infected with BNO69.3 siRNA failed to form tubes (left panel). In addition, BNO69.3 siRNA infected cells became enlarged as shown in FIG. 8 (right panel) as compared to vector-only infected cells (left panel). BNO69.3 siRNA infected cells also lost their ability to proliferate (FIG. 9) and migrate (FIG. 10). The ability of the pro-angiogenic growth factors VEGF and bFGF to rescue HUVECs from the anti-proliferative effects of BNO69.3 siRNA mediated silencing was also assessed. As can be seen in FIG. 11, HUVECs infected with BNO69.3 remained unable to proliferate despite the presence of these growth factors in the culture medium. This observation suggests that BNO69 functions at a point where the VEGF and bFGF signalling pathways converge. This is of significance given the demonstrated ability of tumours to switch between production of angiogenic stimuli like VEGF and bFGF. As a result the tumour has the ability to develop resistance to any drugs targeting either of these two signalling pathways. However drugs targeting BNO69 would account for a tumour's ability to switch between these two angiogenic stimuli.

BNO69.3 siRNA and BNO69.4 siRNA Inhibit Tumour Cell Growth and Migration

The expression of BNO69 isoforms in tumour cell lines (FIG. 12) prompted us to investigate the role of this gene in tumour cell growth. A number of tumour cell lines were infected with virus producing RNAi molecules that silence both BNO69 Isoforms I and III (BNO69.3 siRNA) or silence only the BNO69 Isoform I (BNO69.4 siRNA). These cell lines are representative of different tumour types including breast and brain (FIG. 12).

Figure 13:
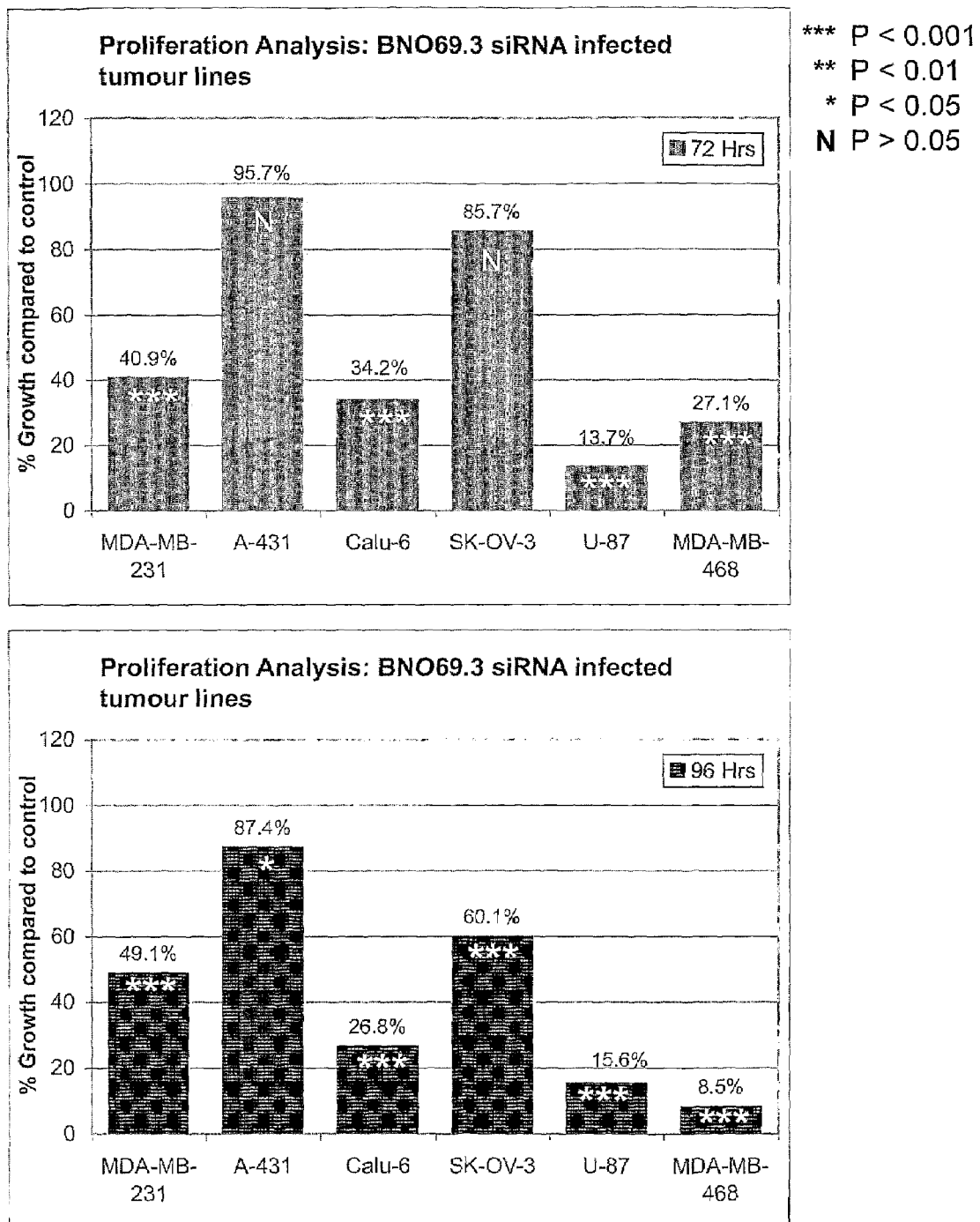
FIG. 13: Analysis of the effect of BNO69.3 (SEQ ID NO: 3) siRNA on proliferation in a range of tumour cell lines.

Infected cell lines were selected for resistance to puromycin (a marker expressed by the viral vector containing the sequence that codes for the shRNA molecules) in order to enrich for cells that express the shRNA molecules under consideration. Following 4 days of selection the cells were transferred to 96 well plates and cultured for 48 hrs with their growth assessed following this culture period. All cancer cells types infected with BNO69.3 siRNA exhibited reduced growth rates (FIG. 13) whereas only a proportion of cancer types exhibited reduced growth in response to the influence of BNO69.4 siRNA (FIG. 14).

Furthermore, we examined the possible influence of BNO69.3 siRNA and BNO69.4 siRNA on the ability of tumour cells to migrate. Migratory behaviour is a hallmark of tumour cell behaviour and underlies tumour metastasis. The potential GAP function of BNO69 would implicate it in signalling pathways that control cell shape and movement. Consequently, it is reasonable to hypothesise that targeting this gene may interfere with cell migration. The breast cancer cell lines (MDA-MB-231 and MDA-MB-468) as well as the U-87 brain glioblastoma cell line infected with BNO69.3 siRNA exhibited significant reduced migration rates whereas only a proportion of cancer types exhibited significant reduced migration in response to the influence of BNO69.4 (FIG. 15).

Figure 16:
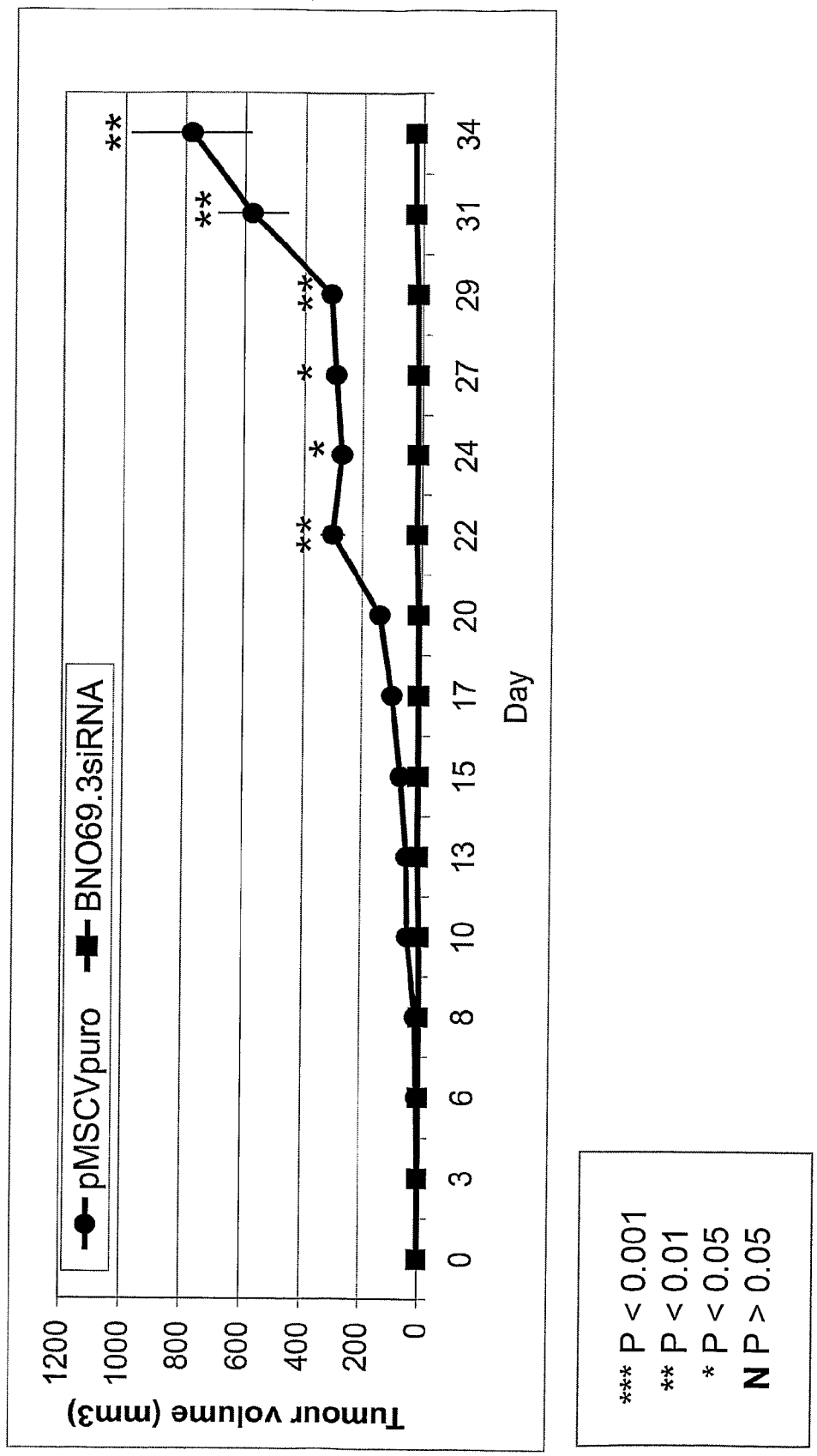
FIG. 16: Analysis of the effect of BNO69.3 (SEQ ID NO: 3) siRNA on MDA-MB-231 orthotopic xenografts in nude mice.

BNO69.3 siRNA and BNO69.4 siRNA Inhibit the Growth of Solid Breast Tumours in Mice The observation that BNO69.3 siRNA and BNO69.4 siRNA curtail the growth and migratory potential of tumour cells in vitro prompted us to investigate the effects of these molecules in the growth of solid tumours in animals. Breast cancer cells (MDA-MB-231) were infected with the viral vectors coding for BNO69.3 siRNA and BNO69.4 siRNA. Following a four day selection in puromycin, to enrich for cells expressing the shRNA molecules under consideration, the cells were injected into the mammary fat pad of immuno-compromised mice (nu/nu mice). Cells infected with the viral vector without the shRNA coding sequences were used as control. The experiment comprised 3 groups of 5 mice per group. Tumour growth was monitored over 34 days, by tumour size measurements every 2-3 days. The data obtained indicate that BNO69.3 dramatically curtails the ability of MDA-MB-231 cells in forming tumours in mice. Comparison with the tumours arising from cells infected with the vector control showed up to 94% reduction in tumour growth as a result of the influence of BNO69.3 siRNA (FIG. 16).

Figure 17:
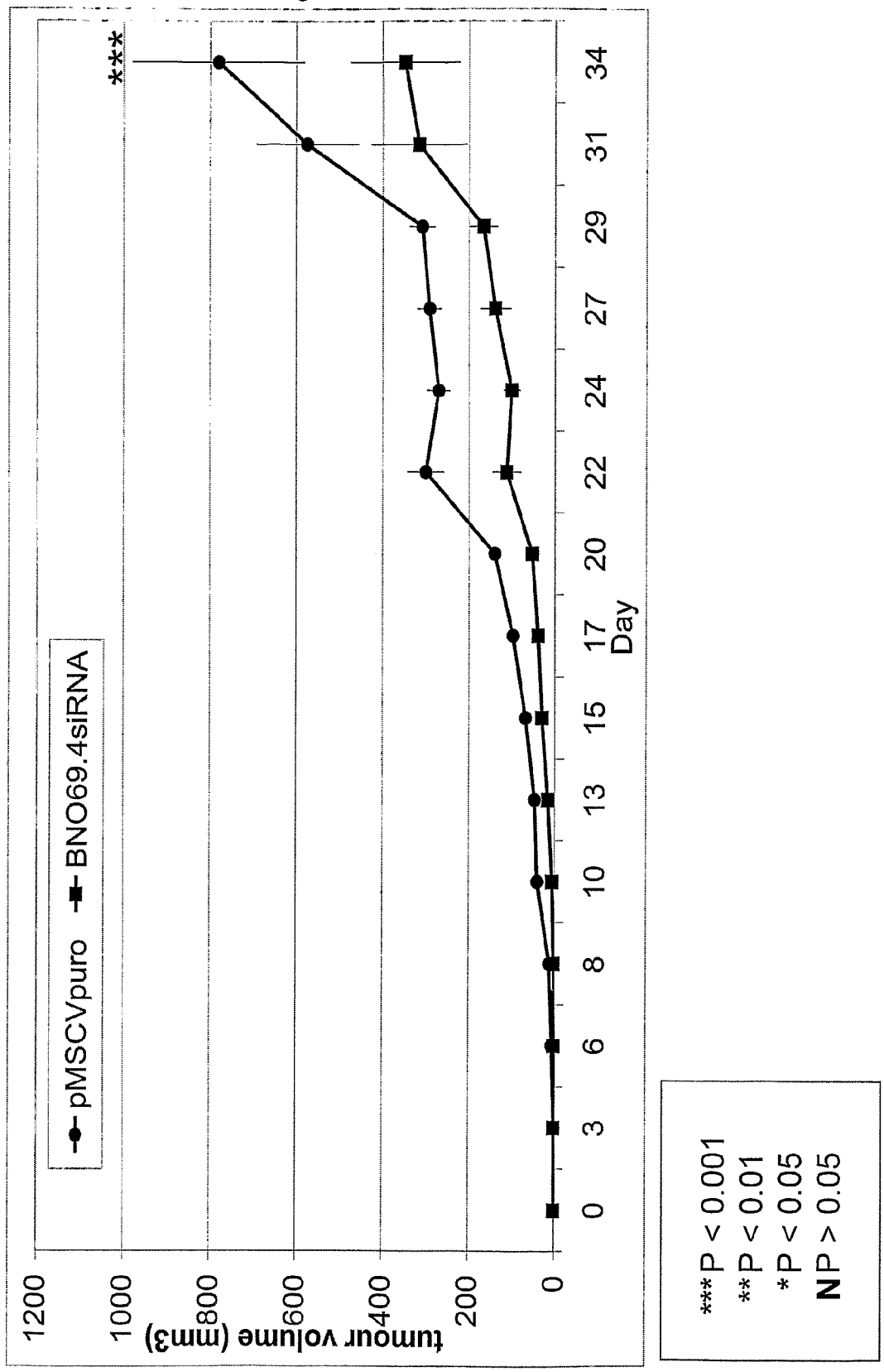
FIG. 17: Analysis of the effect of BNO69.4 (SEQ ID NO: 4) siRNA on MDA-MB-231 orthotopic xenografts in nude mice.

Infection of MDA-MB231 cells with vector coding for BNO69.4 siRNA resulted in statistically significant retardation of solid tumour growth in nude mice but not to the same extent as that seen with BNO69.3 siRNA (FIG. 17).

Together, these results indicate that BNO69 may play a role both in tumour cell growth and tumour angiogenesis. The use of an siRNA to BNO69, and particularly BNO69.3 siRNA and/or BNO69.4 siRNA, in the treatment of angiogenesis-related disorders would therefore encompass the targeting of both tumour cells and endothelial cells.

REFERENCES

The contents of the following documents are incorporated herein by reference:

Altschul, S F. et al. (1997). *Nucleic Acids Res.* 25: 3389-3402.
Augustin, H G. (1998). Trends Pharmacol. Sci. 19: 216-222.
Barrett, T., Xiao, B., Dodson, E J., Dodson, G., Ludbrook, S B., Nurmahomed, K., Gamblin, S J., Musacchio, A., Smerdon, S J., and Eccleston, J F. (1997). Nature 385: 458-461.
Bayless, K J. and Davis, G E., (2002). J. Cell Sci. 115: 1123-1136.
Breaker, R R. and Joyce, G F. (1995). *Chem. Biol.* 2: 655-600.
Chrzanowska-Wodnicka, M., and Burridge, K. (1996). J. Cell Biol. 133: 1403-1415.
Cole, S P. et al. (1984). *Mol. Cell. Biol.* 62: 109-120.
Cote, R J. et al. (1983). *Proc. Natl. Acad. Sci. USA* 80: 2026-2030.
Culver, K. (1996). Gene Therapy: A Primer for Physicians. Second Edition. (Mary Ann Liebert).
Etienne-Manneville, S., and Hall, A. (2002). Nature 420: 629-635.
Friedman, T. (1991). In Therapy for Genetic Diseases. (T Friedman (Ed) Oxford University Press. pp 105-121.
Gamble, J R., Matthias, L J., Meyer, G., Kaur, P., Russ, G., Faull, R., Berndt, M C., and Vadas, M A. (1993). J. Cell Biol. 121: 931-943.
Gamble, J., Meyer, G., Noack, L., Furze, J., Matthias, L., Kovach, N., Harlant, J., and Vadas, M. (1999). Endothelium 7: 23-34.
Goldman, C K. et al. (1997). *Nature Biotechnology* 15: 462-466.
Green, L L. et al. (1994). *Nature Genet.* 7: 13-21.
Hanahan, D. (1997). Science 277: 48-50.
Haseloff, J. and Gerlach, W L. (1988). Nature 334: 585-591.
Heller, R A. et al. (1997). *Proc. Natl. Acad. Sci. USA* 94: 2150-2155.
Hippenstiel, S., Schmeck, B., N'Guessan, P D., Seybold, J., Krull, M., Preissner, K., Eichel-Streiber, C V., and Suttorp, N. (2002). Am. J. Physiol. Lung Cell. Mol. Physiol. 283: L830-L838.
Huse, W D. et al. (1989). *Science* 246: 1275-1281.
Kohler, G. and Milstein, C. (1975). *Nature* 256: 495-497.
Kozbor, D. et al. (1985). *J. Immunol. Methods* 81:31-42.
Lonberg, N. et al. (1994). *Nature* 368: 856-859.
Mackay, D J., and Hall, A. (1998). J. Biol. Chem. 273: 20685-20688.
Meyer, G T., Matthias, L J., Noack, L., Vadas, M A. and Gamble, J R., (1997). Anat. Rec. 249: 327-340.
Musacchio, A., Cantley, L C., and Harrison, S C. (1996). Proc. Natl. Acad. Sci. USA. 93: 14373-14378.

Nobes, C D., and Hall, A. (1999). J. Cell Biol. 144: 1235-1244.

Orlandi, R. et al. (1989). *Proc. Natl. Acad. Sci. USA* 86: 3833-3837.

Rickert, R C. et al. (1997). *Nucleic Acids Res.* 25: 1317-1318.

Rittinger, K., Walker, P A., Eccleston, J F., Smerdon, S J., and Gamblin, S J. (1997). Nature 389: 758-762.

Scharf, D. et al. (1994). *Results Probl. Cell Differ.* 20: 125-162.

Schena, M. et al. (1996). *Proc. Natl. Acad. Sci. USA* 93: 10614-10619.

Schwenk, F. et al. (1995). *Nucleic Acids Res.* 23: 5080-5081.

Van Aelst, L., and D'Souza-Schorey, C. (1997). Genes Dev. 11: 2295-2322.

Winter, G. et al. (1991). *Nature* 349: 293-299.

Wojciak-Stothard, B., Potempa, S., Eichholtz, T., and Ridley, A. J. (2001). J. Cell Sci. 114: 1343-1355.

The invention claimed is:

1. A short interfering RNA (siRNA) molecule comprising a complement of a segment of an mRNA transcribed from the BNO69 gene, wherein said siRNA molecule modulates the expression of BNO69 by RNA interference and said siRNA molecule comprises SEQ ID NO: 3.

2. The siRNA molecule according to claim 1, wherein the siRNA molecule is present within a short hairpin RNA (shRNA) molecule.

3. The siRNA molecule according to claim 2, wherein the shRNA molecule comprises SEQ ID NO: 3 hybridized to its reverse complement.

4. The siRNA molecule according to claim 3, wherein the shRNA molecule is encoded by a nucleic acid molecule comprising SEQ ID NO: 6.

5. A vector encoding the siRNA molecule according to claim 1.

6. The vector of claim 5, wherein the vector comprises SEQ ID NO: 6.

* * * * *

UNITED STATES PATENT AND TRADEMARK OFFICE
CERTIFICATE OF CORRECTION

| | | |
|---|---|---|
| PATENT NO. | : 7,667,028 B2 | Page 1 of 1 |
| APPLICATION NO. | : 11/659756 | |
| DATED | : February 23, 2010 | |
| INVENTOR(S) | : Kremmidiotis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Tenth Day of April, 2012

David J. Kappos
*Director of the United States Patent and Trademark Office*